United States Patent
Kagawa et al.

(10) Patent No.: US 12,358,958 B2
(45) Date of Patent: Jul. 15, 2025

(54) **MUTANT STRAIN OF *TRICHODERMA REESEI* AND METHOD OF PRODUCING PROTEIN USING SAME**

(71) Applicant: Toray Industries, Inc., Tokyo (JP)

(72) Inventors: Yusuke Kagawa, Kamakura (JP); Haruka Saito, Kamakura (JP); Shingo Hiramatsu, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 867 days.

(21) Appl. No.: 17/271,940

(22) PCT Filed: Aug. 28, 2019

(86) PCT No.: PCT/JP2019/033642
§ 371 (c)(1),
(2) Date: Feb. 26, 2021

(87) PCT Pub. No.: WO2020/045472
PCT Pub. Date: Mar. 5, 2020

(65) Prior Publication Data
US 2021/0324018 A1  Oct. 21, 2021

(30) Foreign Application Priority Data
Aug. 29, 2018 (JP) ................................ 2018-160156

(51) Int. Cl.
*C07K 14/37* (2006.01)
*C12N 1/14* (2006.01)
*C12N 9/42* (2006.01)
*C12P 19/00* (2006.01)
*C12R 1/885* (2006.01)

(52) U.S. Cl.
CPC ............... *C07K 14/37* (2013.01); *C12N 1/14* (2013.01); *C12N 9/2437* (2013.01); *C12P 19/00* (2013.01); *C12N 2500/34* (2013.01); *C12R 2001/885* (2021.05)

(58) Field of Classification Search
CPC ........ C07K 14/37; C12N 1/14; C12N 9/2437; C12N 2500/34; C12N 15/80; C12P 19/00; C12R 2001/885
See application file for complete search history.

(56) References Cited

U.S. PATENT DOCUMENTS 8,216,844 B2   7/2012  Bodie et al.
2014/0370546 A1 12/2014 Landowski et al.

FOREIGN PATENT DOCUMENTS

JP       2015-512611       4/2015

OTHER PUBLICATIONS

Martinez et al., Nature Biotechnol., 26(5):553-560 (2008) (Year: 2008).*
Extended European Search Report dated May 13, 2022, of counterpart European Patent Application No. 19854125.2.
H. Ronglin et al., "Trpac1, a pH response transcription regulator, is involved in cellulase gene expression in Trichoderma reesei," Enzyme and Microbial Technology, Stoneham, MA, US, vol. 67, pp. 17-26, Sep. 6, 2014.
A. Schuster et al., "A versatile toolkit for high throughput functional genomics with Trichoderma reesei," Biotechnology for Biotechnology for Biofuels, vol. 5, No. 1, pp. 1-10, Jan. 2, 2012.
Porciuncula, J. de O., "Single Nucleotide Polymorphism Analysis of a Trichoderma reesei Hyper-Cellulolytic Mutant Developed in Japan," Bioscience, Biotechnology, and Biochemistry, vol. 77, 2013, Issue 3, pages cover, 534-543.
Amore, A., "Regulation of Cellulase and Hemicellulase Gene Expression in Fungi," Current Genomics, vol. 14, 2013, pp. 230-249.
Accession No. EGR45828, predicted protein, partial [Trichoderma reesei QM6a], GenBank[online], [retrieved on Nov. 14, 2019], Jul. 25, 2016, Retrieved from the Internet: URL:https://www.ncbi.nlm.nih.gov/protein/EGR45828.1/ , printout: 2 pages.
Accession No. EGR47155, predicted protein [Trichoderma reesei QM6a], GenBank[online], [retrieved on Nov. 14, 2019], Jul. 25, 2016, Retrieved from the Internet:https://www.ncbi.nlm.nih.gov/protein/EGR47155 , printout: 2 pages.
Accession No. ETS02047, hypothetical protein M419DRAFT 98837 [Trichoderma reesei Rut C-30], GenBank[online], [retrieved on Nov. 14, 2019], Mar. 23, 2015, Retrieved from the Internet:https://www.ncbi.nlm.nih.gov/protein/ETS02047 , printout: 2 pages.

* cited by examiner

Primary Examiner — Kade Ariani
(74) Attorney, Agent, or Firm — DLA Piper LLP (US)

(57) ABSTRACT

A mutant strain of *Trichoderma reesei*, the mutant strain having a mutation that eliminates or reduces a function of a polypeptide consisting of the amino acid sequence represented by any of SEQ ID Nos: 4 to 6. A method produces a cellulast, the method including a step of cultivating the mutant strain of *Trichoderma reesei*, the mutant strain having a mutation that eliminates or reduces a function of a polypeptide consisting of the amino acid sequence represented by any of SEQ ID Nos: 4 to 6.

13 Claims, No Drawings
Specification includes a Sequence Listing.

MUTANT STRAIN OF *TRICHODERMA REESEI* AND METHOD OF PRODUCING PROTEIN USING SAME

SEQUENCE LISTING

The instant application contains a Sequence Listing which has been submitted electronically and is hereby incorporated by reference in its entirety. Said electronic copy, created on Feb. 26, 2021, is named 20210226 NBC-21-1095Sequence-Listing.txt and is 84,288 bytes in size.

TECHNICAL FIELD

This disclosure relates to a *Trichoderma reesei* mutant strain having an enhanced protein-producing ability and to a method of protein production using the mutant strain.

BACKGROUND

*Trichoderma reesei* is known to have a high protein-producing ability, and studies have heretofore been made on protein production using *Trichoderma reesei*. *Trichoderma reesei* is especially excellent in terms of the ability to produce a cellulase, which is classified as a saccharifying enzyme, among proteins. For example, to further enhance cellulase production amount, investigations such as overexpression or deletion of a factor that controls cellulase production and investigations on cultivation conditions for cellulase production are being conducted. Juliano P, Single nucleotide polymorphism analysis of a *Trichoderma reesei* hypercellulolytic mutant developed in Japan, Bioscience, Biotechnology, and Biochemistry, Volume 77, 2013, Issue 3, P534-543 describes that a mutant strain of *Trichoderma reesei* which has a high cellulase-producing ability was acquired by reducing the function of Cre1, which is a transcription factor repressing cellulase production, among the cellulase-production-controlling factors of *Trichoderma reesei*.

Meanwhile, Antonella A, Regulation of cellulase and hemicellulose gene expression in fungi, Current Genomics, Volume 14, 2013, P230-249 describes a method of cultivating *Trichoderma reesei* in a culture medium to which glucose or lactose has been added, as a method of improving the production amount of a cellulase of *Trichoderma reesei*.

As described above, a transcription factor which is one of protein-production-controlling factors in *Trichoderma reesei* has been identified, but this is considered to be merely a part of the control mechanism. Thus, it could be helpful to acquire a mutant strain of *Trichoderma reesei* having a further enhanced protein-producing ability by making a search for a novel mechanism controlling protein production by *Trichoderma reesei*, and provide a method of protein production using the mutant strain of *Trichoderma reesei*.

SUMMARY

We wondered whether a gene that had been unknown and was capable of bringing about an increase in protein production could be specified, then the amount of proteins to be produced by *Trichoderma reesei* could be further increased. We thus discovered that an improvement in protein-producing ability can be attained by cultivating a mutant strain of *Trichoderma reesei* in which the function of one or more polypeptides selected from polypeptides consisting of the amino acid sequences represented by SEQ ID NOs: 4, 5, and 6 has been eliminated or reduced.

We thus provide (1) to (15):
(1) A mutant strain of *Trichoderma reesei*, the mutant strain having a mutation that eliminates or reduces a function of a polypeptide consisting of the amino acid sequence represented by any of SEQ ID NOs: 4 to 6.
(2) The mutant strain according to (1), in which the mutation is a mutation that deletes an HSF-type DNA-binding domain of a polypeptide consisting of the amino acid sequence represented by SEQ ID NO: 4.
(3) The mutant strain according to (2), in which the mutation is a frameshift mutation accompanying a mutation in a region nearer to the N-terminal side than the HSF-type DNA-binding domain.
(4) The mutant strain according to (3), in which the mutation is a frameshift mutation due to a mutation in which a histidine residue at the 30th residue from the N-terminal side in the amino acid sequence represented by SEQ ID NO: 4 is changed to a residue of an amino acid other than histidine.
(5) The mutant strain according to (1), in which the mutation is a mutation that deletes a TLD domain of a polypeptide consisting of the amino acid sequence represented by SEQ ID NO: 5.
(6) The mutant strain according to (5), in which the mutation is a frameshift mutation accompanying a mutation in a region nearer to the N-terminal side than the TLD domain.
(7) The mutant strain according to (6), in which the mutation is a frameshift mutation due to a mutation in which a glutamine residue at the 3rd residue from the N-terminal side in the amino acid sequence represented by SEQ ID NO: 5 is changed to a residue of an amino acid other than glutamine.
(8) The mutant strain according to (1), in which the mutation is a mutation of an amino acid sequence of an F-box domain region of a polypeptide consisting of the amino acid sequence represented by SEQ ID NO: 6.
(9) The mutant strain according to (8), in which the mutation is a deletion of the polypeptide consisting of the amino acid sequence represented by SEQ ID NO: 6, the deletion being caused by a frameshift mutation accompanying a mutation of the amino acid sequence of the F-box domain region.
(10) The mutant strain according to (9), in which the mutation is a frameshift mutation due to a mutation in which an alanine residue at the 167th residue from the N-terminal side in the amino acid sequence represented by SEQ ID NO: 6 is changed to a residue of an amino acid other than alanine.
(11) A method of producing a protein, the method including a step of cultivating the mutant strain according to any one of (1) to (10).
(12) A method of producing a protein, the method including a step of cultivating the mutant strain according to any one of (1) to (10), in a culture medium at least including lactose.
(13) A method of producing a cellulase, the method including a step of cultivating the mutant strain according to any one of (1) to (10).
(14) A method of producing a cellulase, the method including a step of cultivating the mutant strain according to any one of (1) to (10), in a culture medium at least including lactose.

(15) A method of producing a sugar, the method including:
- a step of producing a cellulase by the method of producing a cellulase according to (13) or (14); and
- a step of saccharifying a cellulose-containing biomass using the cellulase obtained in the step.

The mutant strain of *Trichoderma reesei* in which the function of a polypeptide consisting of the amino acid sequence represented by any of SEQ ID NOs: 4 to 6 has been eliminated or reduced has an improved protein-producing ability and is capable of highly efficiently producing a protein compared to the parent strain into which the mutation has not been introduced. Furthermore, when the produced proteins are cellulases, an unexpected effect that the cellulases have improved various specific activities is also obtained.

DETAILED DESCRIPTION

Our strains and methods are characterized in that a mutation is introduced into a parent strain of *Trichoderma reesei*, which is a microorganism originally having an excellent protein-producing ability, to thereby further enhance the protein-producing ability. Specifically, we provide a mutant strain of *Trichoderma reesei*, the mutant strain being characterized by having a mutation which eliminates or reduces the function of a polypeptide consisting of the amino acid sequence represented by any of SEQ ID NOs: 4 to 6.

The parent strain of *Trichoderma reesei* is not limited to wild strains, and mutant strains that have been improved to have an increased protein-producing ability can also be favorably used as the parent strain. For example, a mutant strain having an improved protein production property obtained by performing a mutation treatment with a mutagen, UV irradiation or the like can be utilized as the parent strain. Specific examples of mutant strains usable as the parent strain include the following known mutant strains belonging to *Trichoderma reesei*: QM6a strain (NBRC31326), QM9123 strain (ATCC24449), QM9414 strain (NBRC31329), PC-3-7 strain (ATCC66589), QM9123 strain (NBRC31327), RutC-30 strain (ATCC56765), CL-847 strain (Enzyme. Microbiol. Technol., 10, 341-346 (1988)), MCG77 strain (Biotechnol. Bioeng. Symp., 8, 89 (1978)), and MCG80 strain (Biotechnol. Bioeng., 12, 451-459 (1982)). QM6a strain, QM9414 strain, and QM9123 strain are available from NBRC (NITE Biological Resource Center), and PC-3-7 strain and RutC-30 strain are available from ATCC (American Type Culture Collection).

The polypeptide consisting of the amino acid sequence represented by SEQ ID NO: 4 is a polypeptide possessed by *Trichoderma reesei*, and in National Center for Biotechnology Information, this polypeptide has been registered as a predicted protein, partial (EGR45828) that *Trichoderma reesei* QM6a strain has. The polypeptide consisting of the amino acid sequence represented by SEQ ID NO: 4 is a polypeptide whose function is unknown, but Conserved Domain Architecture Retrieval Tool of National Center for Biotechnology Information discloses that the 86th to 186th amino acid residues from the N-terminal side are a heat shock factor (HSF)-type DNA-binding domain. The HSF-type DNA-binding domain is known to have the function of binding to an upstream region of a gene encoding an HSF, which is a transcription factor controlling the expression of a heat shock proteins (Cell, 65 (3), 363-366 (1991)). Specific examples of genes encoding the polypeptide consisting of the amino acid sequence represented by SEQ ID NO: 4 include the base sequence represented by SEQ ID NO: 1.

Examples of methods of eliminating or reducing the function of the polypeptide consisting of the amino acid sequence represented by SEQ ID NO: 4 include a method of introducing a mutation that causes a total deletion of an HSF-type DNA-binding domain, a partial deletion of an HSF-type DNA-binding domain, or a total deletion of the polypeptide consisting of the amino acid sequence represented by SEQ ID NO: 4. Specific examples thereof include a method in which a frameshift mutation or a stop codon mutation is introduced into a gene sequence encoding the polypeptide consisting of the amino acid sequence represented by SEQ ID NO: 4, by a deletion, insertion, substitution or the like of a base.

The phrase "deletion of an HSF-type DNA-binding domain" means a total or partial loss of the domain, a change of the whole or some of the domain into different amino acid(s), or a combination of these. More specifically, that phrase means that the amino acid sequence represented by SEQ ID NO: 4 comes to have a sequence identity of 80% or less with respect to the amino acid sequence of the HSF-type DNA-binding domain. The sequence identity thereto is preferably 50% or less, more preferably 20% or less, more preferably 10% or less, more preferably 5% or less, more preferably 3% or less, more preferably 1% or less, and most preferably 0%.

Specific examples of when the function of a polypeptide consisting of the amino acid sequence represented by SEQ ID NO: 4 is eliminated or reduced by a mutation such as deletion, substitution, or addition, that has occurred in an amino acid sequence located in the HSF-type DNA-binding domain include a mutation in the amino acid sequence represented by SEQ ID NO: 4 which results in a partial or total loss of the region ranging from the 86th to 186th residues from the N-terminal side, which corresponds to the HSF-type DNA-binding domain. Specific examples of such mutations include a mutation in the base sequence represented by SEQ ID NO: 1 which causes a frameshift including insertion of one base residue of guanine into the 85th position. This mutation changes the 30th amino acid residue from the N-terminal side in the amino acid sequence represented by SEQ ID NO: 4 from histidine to threonine. The succeeding frameshift causes the translation to end at the 90th amino acid residue from the N-terminal side and results in loss of the amino acid sequence constituting the HSF-type DNA-binding domain.

The polypeptide consisting of the amino acid sequence represented by SEQ ID NO: 5 is a polypeptide possessed by *Trichoderma reesei*, and in National Center for Biotechnology Information, this polypeptide has been registered as a predicted protein (EGR47155) that *Trichoderma reesei* QM6a strain has. The polypeptide consisting of the amino acid sequence represented by SEQ ID NO: 5 is a polypeptide whose function is unknown, but Conserved Domain Architecture Retrieval Tool of National Center for Biotechnology Information discloses that the 362nd to 553rd amino acid residues from the N-terminal side are a TLD domain. The function of the TLD domain is unknown. Specific examples of genes encoding the polypeptide consisting of the amino acid sequence represented by SEQ ID NO: 5 include the base sequence represented by SEQ ID NO: 2.

Examples of methods of reducing the function of the polypeptide consisting of the amino acid sequence represented by SEQ ID NO: 5 include a method of introducing a mutation that causes a total deletion of a TLD domain, a partial deletion of a TLD domain, or a total deletion of the polypeptide consisting of the amino acid sequence represented by SEQ ID NO: 5. Specific examples thereof include a method in which a frameshift mutation or a stop codon mutation is introduced into a gene sequence encoding the polypeptide consisting of the amino acid sequence represented by SEQ ID NO: 5, by a deletion, insertion, substitution or the like of a base.

The phrase "deletion of a TLD domain" means a total or partial loss of the domain, a change of the whole or some of the domain into different amino acid(s), or a combination of these. More specifically, that phrase means that the amino acid sequence represented by SEQ ID NO: 5 comes to have a sequence identity of 80% or less with respect to the amino acid sequence of the TLD domain. The sequence identity thereto is preferably 50% or less, more preferably 20% or less, more preferably 10% or less, more preferably 5% or less, more preferably 3% or less, more preferably 1% or less, and most preferably 0%.

Specific examples of when the function of a polypeptide consisting of the amino acid sequence represented by SEQ ID NO: 5 is eliminated by a mutation such as deletion, substitution, or addition, that has occurred in an amino acid sequence located in the TLD domain include a mutation in the amino acid sequence represented by SEQ ID NO: 5 which results in a partial or total loss of the region ranging from the 362nd to 553rd residues from the N-terminal side, which corresponds to the TLD domain. Specific examples of such mutations include a frameshift mutation in the base sequence represented by SEQ ID NO: 2 which causes insertion of the 46 base residues represented by SEQ ID NO: 27 into the 6th position. This mutation changes the glutamine residue at the 3rd residue from the N-terminal side in the amino acid sequence represented by SEQ ID NO: 5 into arginine. The translation ends at this position, and the amino acid sequence constituting the TLD domain is lost.

The polypeptide consisting of the amino acid sequence represented by SEQ ID NO: 6 is a polypeptide possessed by *Trichoderma reesei*, and in National Center for Biotechnology Information, this polypeptide has been registered as a predicted protein (EGR48056) that *Trichoderma reesei* QM6a strain has. The polypeptide consisting of the amino acid sequence represented by SEQ ID NO: 6 is a polypeptide whose function is unknown, but Conserved Domain Architecture Retrieval Tool of National Center for Biotechnology Information discloses that the 130th to 172nd amino acid residues from the N-terminal side are an F-box domain. The F-box domain is known to be a domain present in proteins which control the cell cycle (Proc. Natl. Acad. Sci., 95, 2417-2422 (1998)). Specific examples of genes encoding the polypeptide consisting of the amino acid sequence represented by SEQ ID NO: 6 include the base sequence represented by SEQ ID NO: 3.

Examples of methods of reducing the function of the polypeptide consisting of the amino acid sequence represented by SEQ ID NO: 6 include a method of introducing a mutation that causes a total deletion of an F-box domain, a partial deletion of an F-box domain, or a total deletion of the polypeptide consisting of the amino acid sequence represented by SEQ ID NO: 6. Specific examples thereof include a method in which a frameshift mutation or a stop codon mutation is introduced into a gene sequence encoding the polypeptide consisting of the amino acid sequence represented by SEQ ID NO: 6, by a deletion, insertion, substitution or the like of a base.

The phrase "deletion of an F-box domain" means a total or partial loss of the domain, a change of the whole or some of the domain into different amino acid(s), or a combination of these. More specifically, that phrase means that the amino acid sequence represented by SEQ ID NO: 6 comes to have a sequence identity of 80% or less with respect to the amino acid sequence of the F-box domain. The sequence identity thereto is preferably 50% or less, more preferably 20% or less, more preferably 10% or less, more preferably 5% or less, more preferably 3% or less, more preferably 1% or less, and most preferably 0%.

Specific examples of when the function of a polypeptide consisting of the amino acid sequence represented by SEQ ID NO: 6 is eliminated by a mutation such as deletion, substitution, or addition, that has occurred in an amino acid sequence located in the F-box domain include a frameshift mutation in the base sequence represented by SEQ ID NO: 3 which results in a loss of one cytosine base residue which is the 499th residue. This mutation changes the 167th amino acid residue from the N-terminal side in the amino acid sequence represented by SEQ ID NO: 6 from alanine to arginine. The succeeding frameshift causes the translation to end at the 193rd residue from the N-terminal side, resulting in loss of the amino acid sequence constituting the F-box domain.

Another method that may be used to reduce the function of the polypeptide consisting of the amino acid sequence represented by any of SEQ ID NOs: 4 to 6 is to introduce a mutation which diminishes or inhibits the expression of the polypeptide. Specifically, the mutation that diminishes or inhibits the expression of the polypeptide may be one introduced into the promoter or terminator region of a gene encoding the amino acid sequence represented by any of SEQ ID NOs: 4 to 6. In general, the promoter and terminator regions correspond to a region of hundreds of bases in length before and after the gene participating in transcription.

To introduce such mutations into the gene, use can be made of existing genetic mutation methods such as a mutation treatment with a known mutagen or with UV irradiation or the like, gene recombination such as homologous recombination using a selection marker, and a mutation by a transposon.

Our mutant strain is only required to satisfy that the function of at least one or more polypeptides among polypeptides consisting of the amino acid sequences of SEQ ID NOs: 4 to 6 has been eliminated or reduced. The function of two or all of these polypeptides may have been eliminated or reduced. There are no particular limitations on combinations of polypeptides whose functions have been eliminated or reduced, and any of the following mutant strains are included in the mutant strain: a mutant strain of *Trichoderma reesei* in which the functions of the polypeptides consisting of the amino acid sequences represented by SEQ ID NOs: 4 and 5 have been eliminated or reduced; a mutant strain of *Trichoderma reesei* in which the functions of the polypeptides consisting of the amino acid sequences represented by SEQ ID NOs: 4 and 6 have been eliminated or reduced; and a mutant strain of *Trichoderma reesei* in which the functions of the polypeptides consisting of the amino acid sequences represented by SEQ ID NOs: 5 and 6 have been eliminated or reduced.

The mutant strain may be a mutant strain in which the functions of all the three polypeptides consisting of the amino acid sequences represented by SEQ ID NOs: 4 to 6 have been eliminated or reduced. The mutant strain in which the functions of all the three polypeptides consisting of the amino acid sequences represented by SEQ ID NOs: 4 to 6 have been eliminated or reduced can be acquired by subjecting spores of *Trichoderma reesei* as a parent strain to a genetic mutation treatment with nitrosoguanidine (NTG), ethylmethanesulfonic acid (EMS), UV and the like, and analyzing the genes of the resultant mutant strains to collect a mutant strain having the mutation by screening.

Since the mutant strain has an enhanced protein-producing ability compared to the parent strain into which the mutation has not been introduced, a culture solution of the mutant strain has a higher protein concentration than a culture solution obtained by cultivating the parent strain not having the mutation under the same cultivation conditions. When the protein is an enzyme, the enzyme has enhanced specific activity. The increasing rate in protein concentration and the increasing rate in enzyme specific activity are not particularly limited so long as the concentration and the specific activity have increased. It is, however, preferable that the increasing rates are 20% or larger.

Besides having a mutation that eliminates or reduces the function of the polypeptide consisting of the amino acid sequence represented by any of SEQ ID NOs: 4 to 6, our mutant strain may have a mutation which improves protein production amount and/or lowers the viscosity of culture solutions to inhibit the degree of saturation of oxygen dissolved in the culture solutions from decreasing. Specific examples thereof include a genetic mutation which reduces the function of the polypeptide represented by any of SEQ ID NOs: 7, 9, and 11.

The polypeptide consisting of the amino acid sequence represented by SEQ ID NO: 7 is a polypeptide possessed by *Trichoderma reesei* and has been registered at National Center for Biotechnology Information as predicted protein EGR50654 possessed by *Trichoderma reesei* QM6a strain. The polypeptide consisting of the amino acid sequence represented by SEQ ID NO: 7 is a polypeptide whose function is unknown, but Conserved Domain Architecture Retrieval Tool of National Center for Biotechnology Information discloses that the 95th to 277th amino acid residues from the N-terminal side have Middle domain of eukaryotic initiation factor 4G domain (hereinafter referred to as MIF4G domain) and the 380th to 485th amino acid residues from the N-terminal side have MA-3 domain. The two domains, MIF4G and MA-3, are known to have the function of binding to DNAs or RNAs (Biochem., 44, 12265-12272 (2005); Mol. Cell. Biol., 1, 147-156 (2007)). It is presumed from those disclosures that the polypeptide consisting of the amino acid sequence represented by SEQ ID NO: 7 at least has the function of binding to a DNA and/or an RNA.

Specific examples of genes encoding the polypeptide consisting of the amino acid sequence represented by SEQ ID NO: 7 include the base sequence represented by SEQ ID NO: 8. Examples of genetic mutations which reduce the function of EGR50654 include a total deletion of the MIF4G domain and/or MA-3 domain possessed by EGR50654, a partial deletion of the MIF4G domain and/or MA-3 domain, and a genetic mutation which changes the configuration relationship between the MIF4G domain and the MA-3 domain. Furthermore, the function of the polypeptide consisting of the amino acid sequence represented by SEQ ID NO: 7 can be reduced also by introducing a mutation which diminishes or inhibits the expression of the polypeptide. Specific examples of the deletion of the function of the polypeptide consisting of the amino acid sequence represented by SEQ ID NO: 7 include a mutation in the base sequence represented by SEQ ID NO: 8 which deletes any of the 1,039th to 1,044th bases.

The polypeptide consisting of the amino acid sequence represented by SEQ ID NO: 9 is a polypeptide possessed by *Trichoderma reesei* and has been registered at National Center for Biotechnology Information as predicted protein EGR44419 possessed by *Trichoderma reesei* QM6a strain. The polypeptide consisting of the amino acid sequence represented by SEQ ID NO: 9 is a polypeptide whose function is unknown, but Conserved Domain Architecture Retrieval Tool of National Center for Biotechnology Information discloses that the 26th to 499th amino acid residues from the N-terminal side have a Sugar (and other) Transporter domain. It is presumed from this disclosure that the polypeptide consisting of the amino acid sequence represented by SEQ ID NO: 9 at least participates in transport of sugar between the inside and the outside of the fungus bodies.

Specific examples of genes encoding the polypeptide consisting of the amino acid sequence represented by SEQ ID NO: 9 include the base sequence represented by SEQ ID NO: 10. Examples of genetic mutations which reduce the function of EGR44419 include a total deletion of the Sugar (and other) Transporter domain possessed by EGR44419, a partial deletion of the Sugar (and other) Transporter domain, and a genetic mutation which changes the configuration relationship of the Sugar (and other) Transporter domain. Furthermore, the function of the polypeptide consisting of the amino acid sequence represented by SEQ ID NO: 9 can be reduced also by introducing a mutation which diminishes or inhibits the expression of the polypeptide. Specific examples of the deletion of the function of the polypeptide consisting of the amino acid sequence represented by SEQ ID NO: 9 include a mutation in the base sequence represented by SEQ ID NO: 10 which inserts 11 bases at the 1,415th position.

The polypeptide consisting of the amino acid sequence represented by SEQ ID NO: 11 is a polypeptide possessed by *Trichoderma reesei* and has been registered at National Center for Biotechnology Information as EGR48910 of a beta-adaptin large subunit possessed by *Trichoderma reesei* QM6a strain. The polypeptide consisting of the amino acid sequence represented by SEQ ID NO: 11 is one of the proteins that constitute adaptor proteins that bind to clathrin which is widely conserved in eucaryotes, and constitute vesicles that take part in transport inside and outside the cells and inside and outside the fungus bodies (Proc. Nati. Acad. Sci. USA., 101, 14108-14113 (2004)).

Specific examples of genes encoding the polypeptide consisting of the amino acid sequence represented by SEQ ID NO: 11 include the base sequence represented by SEQ ID NO: 12. Examples of genetic mutations for EGR48910 include a mutation in the base sequence represented by SEQ ID NO: 12 which changes the cytosine at the 1,080th base into adenine.

We further provide a method of protein production including a step of cultivating the mutant strain.

In the method of protein production, the protein-producing ability is further enhanced by cultivating the mutant strain in a culture medium containing an inducer. Examples of inducers improving the producibility of, in particular, cellulases include lactose, glucose, cellulose, cellobiose, and xylan. Preferred of these are lactose and/or glucose. Especially preferred is lactose.

In adding an inducer to the culture medium, the inducer may be added at any timing, for example, at initiation of the cultivation or in the middle of the cultivation. However, especially when lactose or glucose is added as an inducer, it is preferred to add the inducer in the middle of the cultivation because this addition enables the effect of improving the protein-producing ability to continue during the cultivation. The amount of lactose to be added per day per L of the culture solution is preferably about 1 g to 50 g, more preferably about 3-25 g, especially preferably about 6-20 g. The amount of glucose to be added per day per L of the culture solution is preferably about 1-200 g, more preferably about 5-100 g, especially preferably about 20-80 g.

In adding cellulose, cellobiose, or xylan as an inducer, biomass containing any of these may be added as an inducer. Specific examples of such biomass include not only plants such as seed plant, pteridophyte, bryophyte, algae, and water plant, but also waste building materials. The seed plants are classified into gymnosperms and angiosperms, and both can be used favorably. The angiosperms are further classified into monocotyledons and dicotyledons. Specific examples of the monocotyledons include bagasse, switchgrass, napier grass, erianthus, corn stover, corncob, rice straw, and wheat straw, and preferred specific examples of the dicotyledons include beet pulp, *eucalyptus*, oak, and white birch.

In using such biomass as an inducer, the biomass may be a pretreated to be used. Methods for the pretreatment are not particularly limited, but, for example, known methods such as acid treatment, sulfuric acid treatment, dilute sulfuric acid treatment, alkali treatment, hydrothermal treatment, sub-critical treatment, fine grinding treatment, and steaming treatment can be used. Pulp may be used as the biomass containing cellulose or xylan, which has been subjected to such a pretreatment.

The composition of the culture medium to be used in the step of cultivating the mutant strain of *Trichoderma reesei* is not particularly limited as long as it is a culture medium composition where the *Trichoderma reesei* can produce a protein, and a known culture medium composition for filamentous fungi of the genus *Trichoderma* can be employed. As a nitrogen source, use can be made, for example, of polypeptone, bouillon, CSL, or soybean cake. The inducer for protein production may be added to the culture medium.

Methods for the cultivation are not particularly limited. For example, the mutant strain can be cultivated by liquid culture in which a centrifuge tube, flask, jar fermenter, tank, or the like is used or solid culture in which a plate or the like is used. It is preferred to cultivate *Trichoderma reesei* under aerobic conditions, and especially preferred among those cultivation methods is submerged culture performed in a jar fermenter or a tank while conducting aeration or stirring. The air flow rate is preferably about 0.1-2.0 vvm, more preferably 0.3-1.5 vvm, especially preferably 0.5-1.0 vvm. The cultivation temperature is preferably about 25-35° C., more preferably 25-31° C. The pH conditions during the cultivation are preferably pH 3.0-7.0, more preferably pH 4.0-6.0. As for cultivation time, the cultivation is conducted under conditions capable of protein production, until the protein is accumulated in a recoverable amount. The cultivation period is usually 24-288 hours, preferably 24-240 hours, more preferably 36-240 hours, still more preferably 36-192 hours.

Although the protein to be produced is not particularly limited, proteins to be excreted from the fungus bodies can be efficiently produced. Preferred of these are enzymes. More preferred are saccharifying enzymes such as cellulases, amylases, invertases, chitinases, and pectinases. Still more preferred are cellulases.

Cellulases that can be produced include various hydrolases, which include enzymes having a decomposition activity against xylan, cellulose, and hemicellulose. Specific examples thereof include cellobiohydrolase (EC 3.2.1.91) which produces cellobiose by hydrolyzing cellulose chains, endoglucanase (EC 3.2.1.4) which hydrolyzes cellulose chains from central portions thereof, β-glucosidase (EC 3.2.1.21) which hydrolyzes cellooligosaccharide and cellobiose, xylanase (EC 3.2.1.8) which is characterized by acting on hemicellulose and, in particular, on xylan, and β-xylosidase (EC 3.2.1.37) which hydrolyzes xylooligosaccharide.

Improvement in protein-producing ability or improvement in cellulase specific activity of our *Trichoderma reesei* mutant strain compared to the parent strain is ascertained by comparing culture solutions obtained by cultivating the mutant strain and the parent strain under the same conditions in protein concentration or in one or more specific activities selected from the group consisting of β-glucosidase specific activity, β-xylosidase specific activity, and cellobiohydrolase specific activity, the protein concentration and the specific activities being determined by the following methods.

The protein concentration is determined in the following manner. Culture solutions of the mutant strain and parent strain are each centrifuged at 15,000×g for 10 minutes to obtain a supernatant. To 250 μL of Quick Start Bradford protein assay (manufactured by Bio-Rad Laboratories, Inc.) is added 5 μL of a diluted cellulase solution. The mixture is allowed to stand still at room temperature for 15 minutes and then examined for absorbance at 595 nm. The concentration of the protein contained in the saccharifying-enzyme solution is calculated on the basis of a calibration curve obtained using bovine serum albumin solutions as reference solutions.

The β-glucosidase specific activity is determined by the following method. First, for the supernatant of the culture solution, 10 μL of an enzyme dilution is added to 90 μL of 50 mM acetate buffer containing 1 mM p-nitrophenyl-β-glucopyranoside (produced by Sigma-Aldrich Japan), and the mixture is allowed to react at 30° C. for 10 minutes. Then, 10 μL of 2 M sodium carbonate is added and mixed well to stop the reaction, and the increase in absorbance at 405 nm is measured. Finally, release of 1 μmol of p-nitrophenol per minute is defined as 1 U of activity to calculate the specific activity.

The β-xylosidase specific activity is determined by the following method. First, for the supernatant of the culture solution, 10 μL of an enzyme dilution is added to 90 μL of 50 mM acetate buffer containing 1 mM p-nitrophenyl-β-xylopyranoside (produced by Sigma-Aldrich Japan), and the mixture is allowed to react at 30° C. for 30 minutes. Then, 10 μL of 2 M sodium carbonate is added and mixed well to stop the reaction, and the increase in absorbance at 405 nm is measured. Finally, release of 1 μmol of p-nitrophenol per minute is defined as 1 U of activity to calculate the specific activity.

The cellobiohydrolase specific activity is determined by the following method. First, for the supernatant of the culture solution, 10 μL of an enzyme dilution is added to 90 μL of 50 mM acetate buffer containing 1 mM p-nitrophenyl-β-lactopyranoside (produced by Sigma-Aldrich Japan), and the mixture is allowed to react at 30° C. for 60 minutes. Then, 10 μL of 2 M sodium carbonate is added and mixed well to stop the reaction, and the increase in absorbance at 405 nm is measured. Finally, release of 1 μmol of p-nitrophenol per minute is defined as 1 U of activity to calculate the specific activity.

Methods of recovering a protein contained in the culture solution where the mutant strain has been cultivated are not particularly limited, but the protein can be recovered by removing the fungus bodies of the mutant strain from the culture solution. Examples of methods of removing the fungus bodies include centrifugation, membrane separation, and filter press.

Furthermore, when the culture solution in which the mutant strain has been cultivated is used as a protein solution without removing the fungus bodies therefrom, the culture solution is preferably treated so that the mutant strain cannot grow therein. Examples of treatment methods of preventing the fungus bodies from growing include heat treatment, chemical treatment, acid/alkali treatment, and UV treatment.

When the protein is an enzyme, the culture solution from which the fungus bodies have been removed or has been treated so that the fungus bodies cannot grow therein, as stated above, can be used directly as an enzyme solution.

When the protein produced by our method is a cellulase, this cellulase can be used to saccharify cellulose-containing biomass to produce a sugar. The cellulase obtained by cultivating the mutant strain is high especially in β-glucosidase specific activity compared to the cellulase obtained by cultivating the parent strain into which the mutation has not been introduced, and can hence efficiently decompose the cellulose-containing biomass to obtain a sugar solution having a high glucose concentration. Thus, a larger quantity of sugar can be obtained.

The cellulose-containing biomass can be either the same biomass as the cellulose-containing biomass mentioned above as an inducer or a pretreated biomass.

Conditions for the saccharification reaction are not particularly limited. The saccharification reaction temperature is preferably 25-60° C., more preferably 30-55° C. The saccharification reaction time is preferably 2-200 hours. The pH in the saccharification reaction is preferably 3.0-7.0, more preferably 4.0-6.0. In cellulases derived from the genus *Trichoderma*, the best pH for the reaction is 5.0. Furthermore, since the pH changes during the hydrolysis, it is preferred to add a buffer to the reaction solution or to conduct the reaction while keeping the pH constant by using an acid or an alkali.

When the enzyme is separated and recovered from the saccharified solution, use can be made of a method in which the saccharified solution is filtered with an ultrafiltration membrane or the like to recover the enzyme on the non-permeation side. According to need, a step of removing solid matter from the saccharified solution may be conducted before the filtration. The recovered enzyme can again be used for a saccharification reaction.

EXAMPLES

Our strains and methods are described specifically below by referring to Examples.

Reference Example 1: Conditions for Protein Concentration Measurement

Protein concentration measuring reagent used: Quick Start Bradford protein assay (produced by Bio-Rad Laboratories, Inc.)
Measuring Conditions
  Measuring temperature: room temperature
  Protein concentration measuring reagent: 250 µL
  Culture solution of filamentous fungus: 5 µL
  Reaction time: 5 min
  Absorbance: 595 nm
  Standard: BSA Reference Example 2: Conditions for Determination of Specific Activity of Cellulases
Conditions for Determination of β-Glucosidase Specific Activity Substrate: p-nitrophenyl-β-glucopyranoside (produced by Sigma-Aldrich Japan)
  Reaction solution: 90 µL of 50 mM acetate buffer containing 1 mM p-nitrophenyl-β-glucopyranoside
  Enzyme dilution: 10 µL
  Reaction temperature: 30° C.
  Reaction time: 10 min
  Reaction terminator: 10 µL of 2 M sodium carbonate
  Absorbance: 405 nm
Conditions for Determination of β-Xylosidase Specific Activity
  Substrate: p-nitrophenyl-β-xylopyranoside (produced by Sigma-Aldrich Japan)
  Reaction solution: 90 µL of 50 mM acetate buffer containing 1 mM p-nitrophenyl-β-xylopyranoside
  Enzyme dilution: 10 µL
  Reaction temperature: 30° C.
  Reaction time: 10 min
  Reaction terminator: 10 µL of 2 M sodium carbonate
  Absorbance: 405 nm
Conditions for Determination of Cellobiohydrolase Specific Activity
  Substrate: p-nitrophenyl-β-lactopyranoside (produced by Sigma-Aldrich Japan)
  Reaction solution: 90 µL of 50 mM acetate buffer containing 1 mM p-nitrophenyl-β-lactopyranoside
  Enzyme dilution: 10 µL
  Reaction temperature: 30° C.
  Reaction time: 10 min
  Reaction terminator: 10 µL of 2 M sodium carbonate
  Absorbance: 405 nm Reference Example 3: Saccharification Test of Cellulose-Containing Biomass As cellulose-containing biomass, use was made of Arbocel (registered trademark) B800 (produced by J. Rettenmaier & Sohne) or bagasse powdered to an average particle diameter of 100 µm. As an enzyme solution, use was made of a filtrate obtained by collecting a 1 mL portion of a culture solution of either a *Trichoderma reesei* mutant strain or the *Trichoderma reesei* parent strain into which the mutation had not been introduced, centrifuging the collected culture solution, recovering a supernatant from which the fungus bodies had been removed, and filtering the supernatant with a 0.22-µm filter.
Saccharification Reaction
  100 µL of a 1 M sodium acetate buffer was used as a buffer for saccharification reaction; 2 µL of 50 g/L erythromycin solution was used to prevent the propagation of various germs; and 0.1 g of Arbocel (registered trademark) B800 (produced by J. Rettenmaier & Sohne) or bagasse powdered to an average particle diameter of 100 µm was used as a material to be saccharified. Enzyme solutions were prepared in the following manner. An enzyme solution obtained by flask cultivation using Arbocel (registered trademark) B800 was introduced in an amount of 150 µL into a measuring cylinder. An enzyme solution obtained by flask cultivation using lactose was introduced in an amount of 300 µL into a measuring cylinder. An enzyme solution obtained by 5 L jar fermenter cultivation was introduced into a measuring cylinder in such an amount as to result in a protein concentration of 0.8 mg. The enzyme solution in each measuring cylinder was diluted with sterilized water to 1 mL in total, and the dilution introduced into a 2 mL tube. A saccharification reaction was conducted under temperature conditions of 50° C. for 24 hours, and the saccharification mixture centrifuged. The resultant supernatant was recovered as a saccharified solution, and the enzymatic reaction terminated by adding 1 N NaOH solution in an amount of one-tenth the amount of the recovered saccharified solution. The glucose concentration in the saccharified solution after the termination of the reaction was determined by the UPLC shown below.

Determination of Glucose Concentration

Glucose was quantitatively analyzed under the following conditions using ACQUITY UPLC System (Waters). The quantitative analysis was performed on the basis of a calibration curve drawn with standard solutions of glucose.

Column: ACQUITY UPLC BEH Amide 1.7 μm 2.1×100 mm Column

Separation method: HILIC

Mobile phase: mobile phase A: 80% acetonitrile, 0.2% aqueous TEA solution, and mobile phase B: 30% acetonitrile, 0.2% aqueous TEA solution, in accordance with the following gradient. The gradient was a linear gradient reaching the mixing ratio corresponding to the time below.

Initiation condition: (A 99.90%, B 0.10%), 2 minutes after initiation: (A 96.70%, B 3.30%), 3.5 minutes after initiation: (A 95.00%, B 5.00%), 3.55 minutes after initiation: (A 99.90%, B 0.10%), 6 minutes after initiation: (A 99.90%, B 0.10%)

Detection method: ELSD (evaporative light scattering detector)

Flow rate: 0.3 mL/min

Temperature: 55° C.

Example 1

Preparation of *Trichoderma reesei* Mutant Strain in which the Function of Polypeptide Consisting of the Amino Acid Sequence Represented by SEQ ID NO: 4 has been Eliminated Method of Preparing Mutant Strain A *Trichoderma reesei* mutant strain in which the function of the polypeptide consisting of the amino acid sequence represented by SEQ ID NO: 4 has been eliminated is prepared in the following manner. A gene represented by SEQ ID NO: 1 that encodes the polypeptide consisting of the amino acid sequence represented by SEQ ID NO: 4 is destroyed by replacing the gene with acetamide as a selection marker and with acetamidase (AmdS) gene (amdS) capable of decomposing acetamide as a selection marker gene. A DNA fragment consisting of the gene sequence represented by SEQ ID NO: 13 is prepared to eliminate the function of the polypeptide consisting of the amino acid sequence represented by SEQ ID NO: 4, and *Trichoderma reesei* ATCC66589 strain is transformed with the DNA fragment, thereby preparing the *Trichoderma reesei* mutant strain in which the function of the polypeptide consisting of the amino acid sequence represented by SEQ ID NO: 4 has been eliminated. By this method, a *Trichoderma reesei* mutant strain is obtained in which the base sequence represented by SEQ ID NO: 1 has been deleted. To allow a DNA fragment consisting of the base sequence represented by SEQ ID NO: 1 to be introduced upstream and downstream an amdS-containing DNA sequence, a plasmid for mutation introduction is prepared to add a portion homologous to the gene sequence of the *Trichoderma reesei* QM9414 strain.

Specifically, PCR is conducted using genomic DNA extracted in a usual manner from the *Trichoderma reesei* QM9414 strain and oligo DNAs represented by SEQ ID NOs: 14 and 15, and the resulting amplified fragment is treated with restriction enzymes AflII and NotI to obtain a DNA fragment for use as the upstream DNA fragment. In addition, PCR is conducted using oligo DNAs represented by SEQ ID NOs: 16 and 17, and the resulting amplified fragment is treated with restriction enzymes MluI and SpeI to obtain a DNA fragment for use as the downstream DNA fragment. The upstream and downstream DNA fragments are introduced into a plasmid to which amdS has been inserted by using restriction enzymes AflII and NotI and restriction enzymes MluI and SpeI, respectively, to construct a plasmid for mutation introduction. The plasmid for mutation introduction is treated with restriction enzymes AflII and SpeI, and the *Trichoderma reesei* ATCC66589 strain is transformed with the obtained DNA fragment which is shown by SEQ ID NO: 13. The manipulations involving the molecular biological technique are performed as described in Molecular cloning, laboratory manual, 1st, 2nd, 3rd (1989). In addition, the transformation is carried out using a standard technique, i.e., a protoplast PEG method, and specifically, is performed as described in Gene, 61, 165-176 (1987).

Preparation and Evaluation of the Mutant Strain

The *Trichoderma reesei* mutant strain obtained by the method described above was used as *Trichoderma reesei* mutant strain I in the following protein production test and experiments to determine protein concentration and cellulase specific activity.

Example 2

Preparation of *Trichoderma reesei* Mutant Strain in which the Function of Polypeptide Consisting of the Amino Acid Sequence Represented by SEQ ID NO: 5 has been Eliminated Method of Preparing Mutant Strain A *Trichoderma reesei* mutant strain in which the function of the polypeptide consisting of the amino acid sequence represented by SEQ ID NO: 5 has been eliminated is prepared in the following manner. A gene represented by SEQ ID NO: 2 that encodes the polypeptide consisting of the amino acid sequence represented by SEQ ID NO: 5 is destroyed by replacing the gene with acetamide as a selection marker and with acetamidase (AmdS) gene (amdS) capable of decomposing acetamide as a selection marker gene. A DNA fragment consisting of the gene sequence represented by SEQ ID NO: 18 is prepared to eliminate the function of the polypeptide consisting of the amino acid sequence represented by SEQ ID NO: 5, and *Trichoderma reesei* ATCC66589 strain is transformed with the DNA fragment, thereby preparing the *Trichoderma reesei* mutant strain in which the function of the polypeptide consisting of the amino acid sequence represented by SEQ ID NO: 5 has been eliminated. By this method, a *Trichoderma reesei* mutant strain is obtained in which the base sequence represented by SEQ ID NO: 2 has been deleted. To allow a DNA fragment consisting of the base sequence represented by SEQ ID NO: 2 to be introduced upstream and downstream an amdS-containing DNA sequence, a plasmid for mutation introduction is prepared to add a portion homologous to the gene sequence of the *Trichoderma reesei* QM9414 strain.

Specifically, a synthesized DNA fragment shown by SEQ ID NO: 19 is treated with restriction enzymes AflII and NotI to obtain a DNA fragment for use as the upstream DNA fragment. In addition, PCR is conducted using genomic DNA extracted in a usual manner from the *Trichoderma reesei* QM9414 strain and oligo DNAs represented by SEQ ID NOs: 20 and 21, and the resulting amplified fragment is treated with restriction enzymes Mlul and Spel to obtain a DNA fragment for use as the downstream DNA fragment. The upstream and downstream DNA fragments are introduced into a plasmid to which amdS has been inserted by using restriction enzymes AflII and NotI and restriction enzymes Mlul and Spel, respectively, to construct a plasmid for mutation introduction. The plasmid for mutation introduction is treated with restriction enzymes AflII and Spel, and the *Trichoderma reesei* ATCC66589 strain is transformed with the obtained DNA fragment which is shown by SEQ ID NO: 18. The manipulations involving the molecular biological technique are performed as described in Molecular cloning, laboratory manual, 1st, 2nd, 3rd (1989). In addition, the transformation is carried out using a standard technique, i.e., a protoplast PEG method, and specifically, is performed as described in Gene, 61, 165-176 (1987).

Preparation and Evaluation of the Mutant Strain

The *Trichoderma reesei* mutant strain obtained by the method described above was used as *Trichoderma reesei* mutant strain II in the following protein production test and experiments to determine protein concentration and cellulase specific activity.

Example 3

Preparation of *Trichoderma reesei* Mutant Strain in which the Function of Polypeptide Consisting of the Amino Acid Sequence Represented by SEQ ID NO: 6 has been Eliminated Method of Preparing Mutant Strain A *Trichoderma reesei* mutant strain in which the function of the polypeptide consisting of the amino acid sequence represented by SEQ ID NO: 6 has been eliminated is prepared in the following manner. A gene represented by SEQ ID NO: 3 that encodes the polypeptide consisting of the amino acid sequence represented by SEQ ID NO: 6 is destroyed by replacing the gene with acetamide as a selection marker and with acetamidase (AmdS) gene (amdS) capable of decomposing acetamide as a selection marker gene. A DNA fragment consisting of the gene sequence represented by SEQ ID NO: 22 is prepared to eliminate the function of the polypeptide consisting of the amino acid sequence represented by SEQ ID NO: 6, and *Trichoderma reesei* ATCC66589 strain is transformed with the DNA fragment, thereby preparing the *Trichoderma reesei* mutant strain in which the function of the polypeptide consisting of the amino acid sequence represented by SEQ ID NO: 6 has been eliminated. By this method, a *Trichoderma reesei* mutant strain is obtained in which the base sequence represented by SEQ ID NO: 3 has been deleted. To allow a DNA fragment consisting of the base sequence represented by SEQ ID NO: 3 to be introduced upstream and downstream an amdS-containing DNA sequence, a plasmid for mutation introduction is prepared to add a portion homologous to the gene sequence of the *Trichoderma reesei* QM9414 strain.

Specifically, PCR is conducted using genomic DNA extracted in a usual manner from the *Trichoderma reesei* QM9414 strain and oligo DNAs represented by SEQ ID NOs: 23 and 24, and the resulting amplified fragment is treated with restriction enzymes AflII and NotI to obtain a DNA fragment for use as the upstream DNA fragment. In addition, PCR is conducted using oligo DNAs represented by SEQ ID NOs: 25 and 26, and the resulting amplified fragment is treated with restriction enzymes Mlul and Xhol to obtain a DNA fragment for use as the downstream DNA fragment. The upstream and downstream DNA fragments are introduced into a plasmid to which amdS has been inserted by using restriction enzymes AflII and NotI and restriction enzymes Mlul and Xhol, respectively, to construct a plasmid for mutation introduction. The plasmid for mutation introduction is treated with restriction enzymes AflII and Spel, and the *Trichoderma reesei* ATCC66589 strain is transformed with the obtained DNA fragment which is shown by SEQ ID NO: 22. The manipulations involving the molecular biological technique are performed as described in Molecular cloning, laboratory manual, 1st, 2nd, 3rd (1989). In addition, the transformation is carried out using a standard technique, i.e., a protoplast PEG method, and specifically, is performed as described in Gene, 61, 165-176 (1987).

Preparation and Evaluation of the Mutant Strain

The *Trichoderma reesei* mutant strain obtained by the method described above was used as *Trichoderma reesei* mutant strain III in the following protein production test and experiments for determining protein concentration and cellulase specific activity.

Example 4

Protein Production Test Using *Trichoderma reesei* Mutant Strains
Preculture

After spores of each of the *Trichoderma reesei* mutant strains prepared in Examples 1 to 3 are diluted with physiological saline to be $1.0 \times 10^7$/mL, 2.5 mL of the diluted spore solution is inoculated into 250 mL of the preculture medium shown in Table 1 that has been placed in a 1 L baffled flask, and incubated on a shaker under the conditions of 28° C. and 120 rpm for 72 hours. *Trichoderma reesei* ATCC66589 strain is used as a control to conduct the same experiments shown below.

TABLE 1

| | |
|---|---|
| Glucose | 20 g |
| 5× Mandel's solution* | 200 mL |
| 10× Ammonium tartrate solution** | 100 mL |
| Corn steep liquor | 50 g |
| Trace element solution*** | 1 mL |
| Tween 80 | 0.5 mL |
| PE-M | 1 mL |
| | (per 1 L) |

*The 5× Mandel's solution has the following composition.
7 g/L $(NH_4)_2SO_4$
10 g/L $KH_2PO_4$
2 g/L $CaCl_2 \cdot 2H_2O$
1.5 g/L $MgSO_4 \cdot 7H_2O$
**The 10× Ammonium tartrate solution contains 92 g/L ammonium tartrate.
***The trace element solution has the following composition.
0.3 g/L $H_3BO_3$
1.3 g/L $(NH_4)_6Mo_7O_{24} \cdot 4H_2O$
5 g/L $FeCl_3 \cdot 6H_2O$
2 g/L $CuSO_4 \cdot 5H_2O$
0.4 g/L $MnCl_2 \cdot 4H_2O$
10 g/L $ZnCl_2$ Main Culture Arbocel (registered trademark) B800 is added to the main-culture medium shown in Table 2, and an investigation of submerged culture is conducted using a 5 L jar fermenter (manufactured by ABLE & Biott Co., Ltd.).

The preculture solutions of the *Trichoderma reesei* ATCC66589 strain and the *Trichoderma reesei* mutant strains prepared in Examples 1, 2, and 3 are each inoculated in an amount of 200 mL into 2 L of the main-culture medium to which Arbocel (registered tradename) B800 has been added.

After inoculation of each preculture medium into the main-culture medium, submerged culture is performed under the cultivation conditions of 28° C., 700 rpm, and an air flow rate of 100 mL/min while regulating the pH to 5.0.

TABLE 2

| | |
|---|---|
| Arbocel B800 (produced by J. Rettenmaier & Sohne) | 100 g |
| 5× Mandel's solution* | 200 mL |
| Corn steep liquor | 25 g |
| Trace element solution*** | 1 mL |
| Tween 80 | 0.5 mL |
| PE-M | 1 mL |
| | (per 1 L) |

*Same as in Table 1.
***Same as in Table 1.

Addition of Liquid Sugar During Main Culture

At 40 hours after initiation of the main culture, the liquid sugar culture medium shown in Table 3 is continuously added to the main-culture solution in an amount of 250 mL per day.

TABLE 3

| | |
|---|---|
| Glucose | 500 g |
| Lactose | 125 g |
| $(NH_4)_2SO_4$ | 8.75 g |
| | (per 1 L) |

Collection of Culture Solutions

At each of given time periods after initiation of the cultivation, 20 mL portion of each of the main-culture solutions of the *Trichoderma reesei* mutant strains prepared in Examples 1 to 3 is collected. A part of the collected culture solution is centrifuged under the conditions of 15,000×g and 4° C. for 10 minutes to obtain a supernatant. The supernatant is filtered with a 0.22 μm filter, and the filtrate is used as a cellulase solution in the following experiments.

Determination of Protein Concentration

The protein concentration of each of the culture solutions of Examples 1 to 3 which have been collected at intervals after initiation of the cultivation is determined under the conditions shown in Reference Example 1. As a result, the *Trichoderma reesei* mutant strains prepared in Examples 1 to 3 give culture solutions having higher protein concentrations, in terms of relative value, than that of the *Trichoderma reesei* ATCC66589 strain.

Determination of Enzyme Activities

The culture solutions of Examples 1 to 3 that have been collected at intervals after initiation of the cultivation are used as enzyme solutions to determine the specific activities of β-glycosidase, β-xylosidase, and cellobiohydrolase under the conditions shown in Reference Example 2. In determining the specific activity, an increase in absorbance at 405 nm is measured, and release of 1 μmol of the substrate per minute is defined as 1 U of activity to calculate the specific activity. As a result, the culture solutions of the *Trichoderma reesei* mutant strains prepared in Examples 1 to 3 are higher in the three specific activities than the culture solution of the *Trichoderma reesei* ATCC66589 strain.

Flask Cultivation

Spores of each of the *Trichoderma reesei* mutant strains I to III prepared in Examples 1 to 3 were diluted with physiological saline to be $1.0×10^7$/mL, and 0.1 mL of the resultant spore dilution was inoculated into 10 mL of the flask culture medium containing Arbocel (registered trademark) B800 or lactose shown in Table 4, that had been placed in a 50 mL baffled flask. This spore dilution was incubated on a shaker under the conditions of 28° C. and 120 rpm for 120 hours.

Furthermore, the *Trichoderma reesei* ATCC66589 strain, which was the parent strain into which any of the mutations of mutant strains I to III had not been introduced, was subjected to 120 hours incubation by the method shown above, as a control for the mutant strains.

TABLE 4

| | |
|---|---|
| Arbocel B800 (produced by J. Rettenmaier & Sohne) Or | 20 g |
| Lactose (produced by Kanto Chemical Co., Inc.) | 20 g |
| 5× Mandel's solution* | 200 mL |
| 10× Ammonium tartrate solution** | 100 mL |
| Corn steep liquor | 50 g |
| Trace element solution*** | 1 mL |
| Tween 80 | 0.5 mL |
| PE-M | 1 mL |
| | (per 1 L) |

*Same as in Table 1.
**Same as in Table 1.
***Same as in Table 1.

Collection of Culture Solutions

At 120 hours after initiation of the flask cultivation, 1 mL portion of each culture solution was collected. The culture solution was centrifuged under the conditions of 15,000×g and 4° C. for 10 minutes to obtain a supernatant. The supernatant was filtered with a 0.22 μm filter, and the filtrate was used in the following experiments.

Determination of Protein Concentration

In the flask cultivation using Arbocel (registered trademark) B800, when the protein concentration in the culture solution obtained by cultivating the *Trichoderma reesei* ATCC66589 strain was taken as 1, then the relative values of the protein concentrations in the culture solutions of *Trichoderma reesei* mutant strains I, II, and III were 1.1 each. It was thus ascertained that the mutant strains had a higher protein-producing ability than the parent strain.

Also in the flask cultivation using lactose, when the protein concentration in the culture solution obtained by cultivating the *Trichoderma reesei* ATCC66589 strain was taken as 1, then the protein concentration for *Trichoderma reesei* mutant strain I was 1.2, for mutant strain II was 1.3, and for mutant strain III was 1.2. It was thus ascertained that the mutant strains had a higher protein-producing ability than the parent strain.

Determination of Various Cellulase Specific Activities

In the flask cultivation using Arbocel (registered trademark) B800, when various cellulase specific activities of the culture solution obtained by cultivating the *Trichoderma reesei ATCC66589* strain were taken as 1, then the β-glucosidase specific activities were 1.1 for *Trichoderma reesei* mutant strain I, 1.2 for mutant strain II, and 1.1 for mutant strain III, the β-xylosidase specific activity was 1.1 for all the *Trichoderma reesei* mutant strains I, II, and III, and the cellobiohydrolase specific activity was also 1.1 for all the mutant strains I, II, and III. It was thus ascertained that the mutant strains had the unexpected effect of bringing about improvements in various cellulase specific activities.

Also in the flask cultivation using lactose, when various cellulase specific activities of the culture solution obtained by cultivating the *Trichoderma reesei* ATCC66589 strain were taken as 1, then the β-glucosidase specific activities were 1.1 for *Trichoderma reesei* mutant strain I, 1.2 for mutant strain II, and 1.4 for mutant strain III, the β-xylosidase specific activities were 1.1 for *Trichoderma reesei* mutant strain I, 1.4 for mutant strain II, and 1.4 for mutant strain III, and the cellobiohydrolase specific activities were 1.2 for mutant strain I, 1.1 for mutant strain II, and 1.1 for mutant strain III. It was thus ascertained that the mutant strains had the unexpected effect of bringing about improvements in various cellulase specific activities.

Saccharification Reaction Test

In accordance with the technique described in Reference Example 3, culture solutions collected at 120 hours after initiation of the flask cultivation of *Trichoderma reesei* mutant strains I, II, and III were used as cellulases to conduct a saccharification reaction test of cellulose-containing biomass. As the cellulose-containing biomass, Arbocel (registered trademark) B800 or powdered bagasse was used.

As a result, in the saccharification reaction for saccharifying Arbocel (registered trademark) B800, when the glucose concentration in the saccharified solution obtained using the cellulases obtained from the *Trichoderma reesei* ATCC66589 strain by the flask cultivation using lactose was taken as 1, then the relative value of the glucose concentration in the saccharified solution obtained using the cellulases obtained from *Trichoderma reesei* mutant strain I was 1.2, the relative value of the glucose concentration in the saccharified solution obtained using the cellulases obtained from mutant strain II was 1.3, and the relative value of the glucose concentration in the saccharified solution obtained using the cellulases obtained from mutant strain III was 1.1. Meanwhile, when the glucose concentration in the saccharified solution obtained using the cellulases obtained from *Trichoderma reesei* ATCC66589 strain by the flask cultivation using Arbocel (registered trademark) B800 was taken as 1, then the relative value of the glucose concentration in the saccharified solution obtained using the cellulases obtained from *Trichoderma reesei* mutant strain I was 1.1, the relative value of the glucose concentration in the saccharified solution obtained using the cellulases obtained from mutant strain II was 1.2, and the relative value of the glucose concentration in the saccharified solution obtained using the cellulases obtained from mutant strain III was 1.1.

In the saccharification reaction for saccharifying powdered bagasse, when the glucose concentration in the saccharified solution obtained using the cellulases obtained from the *Trichoderma reesei* ATCC66589 strain by the flask cultivation using lactose was taken as 1, then the relative value of the glucose concentration in the saccharified solution obtained using the cellulases obtained from *Trichoderma reesei* mutant strain I was 1.3, the relative value of the glucose concentration in the saccharified solution obtained using the cellulases obtained from mutant strain II was 1.3, and the relative value of the glucose concentration in the saccharified solution obtained using the cellulases obtained from mutant strain III was 1.1. Meanwhile, when the glucose concentration in the saccharified solution obtained using the cellulases obtained from *Trichoderma reesei* ATCC66589 strain by the flask cultivation using Arbocel (registered trademark) B800 was taken as 1, then the relative value of the glucose concentration in the saccharified solution obtained using the cellulases obtained from *Trichoderma reesei* mutant strain I was 1.2, the relative value of the glucose concentration in the saccharified solution obtained using the cellulases obtained from mutant strain II was 1.3, and the relative value of the glucose concentration in the saccharified solution obtained using the cellulases obtained from mutant strain III was 1.1.

It was ascertained from those results that the cellulases produced by each of the *Trichoderma reesei* mutant strains I to III were superior in enzymatic activity to the cellulases produced by the parent strain and hence had an excellent ability to produce glucose from cellulose-containing biomass.

Example 5

Preparation of *Trichoderma reesei* Mutant Strain in which the Functions of Polypeptides Consisting of Amino Acid Sequences Represented by SEQ ID NOs: 4, 5, and 6 have been Eliminated A QM9414-A strain, which was a strain obtained by passage culture of *Trichoderma reesei* QM9414 strain, was subjected to a genetic mutation treatment to acquire a QM9414-B strain as a mutant strain. The genetic mutation treatment was conducted in the following manner. Spores of the QM9414-A strain were inoculated into the preculture medium shown in Table 1 so that $1.0 \times 10^5$ spores were inoculated per mL of the preculture medium. 15 mL of the preculture medium was incubated for a half day and then centrifuged to recover the spores. The recovered spores were suspended in a Tris-maleate buffer (pH 6.0) to give a 10 mL spore solution, and 0.5 mL of an NTG solution obtained by dissolution with a Tris-maleate buffer (pH 6.0) to result in a concentration of 1.0 g/L was added thereto. The resultant mixture was held at 28° C. for 100 minutes to perform the genetic mutation treatment. The spores that had undergone the genetic mutation treatment were recovered by centrifuging, subsequently rinsed with a Tris-maleate buffer (pH 6.0) three times, and finally suspended as genetic-mutation-treated spores in 10 mL of a Tris-maleate buffer (pH 6.0). Subsequently, the genetic-mutation-treated spores were added to an agar medium prepared by adding crystalline cellulose. The size of halos that surrounded colonies and indicated regions where the crystalline cellulose had been decomposed by cellulases was used as an index to select a QM9414-B strain which had formed a large halo.

The QM9414-B strain was genetically analyzed and, as a result, was ascertained to have undergone the following mutations in the base sequences represented by SEQ ID NOs: 1, 2, and 3.

In the base sequence represented by SEQ ID NO: 1, one guanine base residue had been inserted into the 85th position. This mutation changed the 30th amino acid residue from the N-terminal side in the amino acid sequence represented by SEQ ID NO: 4 from histidine to threonine, and the succeeding frameshifts caused the translation to end at the 90th amino acid residue from the N-terminal side.

In the base sequence represented by SEQ ID NO: 2, 46 base residues represented by SEQ ID NO: 27 had been inserted into the 6th position. This mutation changed the glutamine residue at the 3rd residue from the N-terminal side in the amino acid sequence represented by SEQ ID NO: 5 into arginine and caused the translation to end at that position.

In the base sequence represented by SEQ ID NO: 3, the one cytosine base residue at the 499th residue had been deleted. This mutation changed the 167th amino acid residue from the N-terminal side in the amino acid sequence represented by SEQ ID NO: 6 from alanine to arginine, and the succeeding frameshifts caused the translation to end at the 193rd position from the N-terminal side.

Example 6

Protein Production Test Using *Trichoderma reesei* QM9414-B Strain

The mutant strain QM9414-B strain obtained in Example 5 was cultivated in accordance with the (Preculture), (Main Culture), (Addition of Liquid Sugar during Main Culture), and (Collection of Culture Solutions) described in Example 4, and the protein concentration was determined under the conditions shown in Reference Example 1. The parent strain QM9414-A strain was used as a control and cultivated in the same manner as for the QM9414-B strain, and the protein concentration was determined under the conditions shown in Reference Example 1.

The produced-protein concentrations at 120 hours after initiation of the cultivation were determined and, as a result, the QM9414-B strain gave an increased relative value which was 1.2 times higher than that of the QM9414-A strain. Likewise, the protein concentrations at 200 hours after initiation of the cultivation were determined. As a result, the QM9414-A strain gave a protein concentration which was unchanged from that obtained at 120 hours after initiation of the cultivation, whereas the QM9414-B strain gave an increased protein concentration which was 1.3 times higher than the protein concentration obtained at 120 hours after initiation of the cultivation.

When the protein concentration given by the QM9414-A strain at 120 hours after initiation of the cultivation was taken as 1, the relative value of the protein concentration given by the QM9414-B strain was 1.8. When the protein concentration given by the QM9414-A strain at 185 hours after initiation of the cultivation was taken as 1, the relative value of the protein concentration given by the QM9414-B strain was 2.7.

The invention claimed is:

1. A mutant strain of *Trichoderma reesei*, the mutant strain having a mutation in a gene encoding a polypeptide consisting of an amino acid sequence of SEQ ID NO: 4 that eliminates an expression of the polypeptide consisting of the amino acid sequence of SEQ ID NO: 4, wherein the mutation is a mutation that deletes a heat shock factor (HSF)-type DNA-binding domain of the polypeptide consisting of the amino acid sequence of SEQ ID NO: 4.

2. The mutant strain according to claim 1, wherein the mutation is a frameshift mutation causing a mutation in a region nearer to the N-terminal side than the HSF-type DNA-binding domain.

3. A mutant strain of *Trichoderma reesei*, the mutant strain having a mutation in a gene encoding a polypeptide consisting of an amino acid sequence of SEQ ID NO: 4 that eliminates an expression of the polypeptide consisting of the amino acid sequence of SEQ ID NO: 4.

4. The mutant strain of claim 3, wherein the mutation results in the deletion of the gene encoding the polypeptide consisting of the amino acid sequence of SEQ ID NO: 4.

5. The mutant strain according to claim 2, wherein the mutation is a frameshift mutation due to a mutation in which a histidine residue at the 30th residue from the N-terminal side in the amino acid sequence of SEQ ID NO: 4 is changed to a residue of an amino acid other than histidine.

6. A method of producing a protein, the method comprising a step of cultivating the mutant strain according to claim 1 or 4.

7. A method of producing a protein, the method comprising a step of cultivating the mutant strain according to claim 1 or 4, in a culture medium at least comprising lactose.

8. The method of producing a protein according to claim 6, wherein, in the cultivation step, at least one selected from the group consisting of lactose and glucose is added to a culture medium in the middle of a cultivation.

9. A method of producing a cellulase, the method comprising a step of cultivating the mutant strain according to claim 1 or 4.

10. A method of producing a cellulase, the method comprising a step of cultivating the mutant strain according to claim 1 or 4, in a culture medium at least comprising lactose.

11. The method of producing a cellulase according to claim 9, wherein, in the cultivation step, at least one selected from the group consisting of lactose and glucose is added to a culture medium in the middle of a cultivation.

12. A method of producing a sugar, the method comprising:
a step of producing a cellulase by the method of producing a cellulase according to claim 9; and
a step of saccharifying a cellulose-containing biomass using the cellulase obtained in the step.

13. The mutant strain of claim 1, wherein the mutation results in a partial or total loss of a region ranging from the 86th to 186th residues from the N-terminal side of SEQ ID NO: 4, which corresponds to the HSF-type DNA-binding domain.

* * * * *

SEQUENCE LISTING

```
<160> NUMBER OF SEQ ID NOS: 27

<210> SEQ ID NO 1
<211> LENGTH: 1975
<212> TYPE: DNA
<213> ORGANISM: Trichoderma reesei

<400> SEQUENCE: 1
cctaccatca gcatgtctcc accgagtccc gtcgaccatc cgatggaggg cacgtcgcca        60
gaggacaact cgcccacggg ccacggccac ggctccggct ccgaccccga aggcagctcc       120
aatggcaagc cgcccgtctc ccgggccggc aacgcatcgc cgcaggagca cggcgccctc       180
accacctcga gcaacatgcc cgcccctcct cccgccgccg ccgctgctgt tcaccagccc       240
aagatcgtcc agactgcctt tatccataag ctatacaagt gaggaccctg gcctccctct       300
ctcccccaaa cccccctttc cccttcaat gcttccttga cctgccaagg agggccccga        360
gactaaagcg acagctgcta acggcgcaaa tagcatgttg gaagacacca gtatacagca       420
tctcatatcc tggtcatcgt ccgccgaaag cttcgtcatg tcgccctctg ccgacttctc       480
caaggtatta tcgtaagcag tgccccgaca atcctcgccc tttctggcc aattcgctca        540 ttctcgcccc cagacaatac ttcaaacaca ccaacatatc gtctttcgtg cgtcagctca       600
acatgtacgg attccataaa ggtacctcct gcccccgctt gcttctgcct cgaacctccg       660
aacctcgaat ggcttaccat ggatgcagaa cgagacgtgt ttcataccgg caaccccgaa       720
acgacgctct gggaattcaa gcacggcaac ggcaacttca agcgcggcga cctcgtcggc       780
cttcgagaga tcaagcgtcg cgccagccga cacgctctcg tcaaccggga aaacaccttt       840
cccaagacct ccacatctca gcctggcacg cccattgagc ctgttcaagt cccgccggat       900
agcatcgagg ctagaatagc caacctggag cactccctgt acgatacggc tgcgagactg       960
cagagaagcg aggaatcggc ccactacatg catgtcaaga accaggccat catggagaca      1020
ctcaaccgac tgctcttctt caaccaagag ttgtccaagg ggatactgtc gcttgtacct      1080
ccagacaacc ctgtacacag agatggtttg tcacacgaaa caatcaggac gatacgctat      1140
tcatgggaga cgatgaaact gacaatgagg gcttcaagtc atgacactcc agggcgaaat      1200
ggtgaggcag gcagaaatgc tgcgctcgct cgacgagccg cacgagcctg tctattccgc      1260
caggcaacag ttcttcggca cggtcgacaa cgcccccgtg tccccgcggc agcttcctca      1320
agacgacaac aggcgagtca cgctcaacgt tccgcagggc cggagtcagc cgtcgtaccg      1380
```

```
accagccgtc ccctcgaacc tgtccgccgg cacgcggcga ccctacggat ccatcagcgg    1440
cggtgccggc tcctcacctc tgcgcaatgc cgcgccggca cccccagcag ggccgcatcc    1500
cctttccaac gtggagaccg tccccagcaa cctggccaga cgccataccg ccgcagacat    1560
tcgcgcacac ggatggcagc ccaacgcacc gccttatccc cctggagccg tgccgccgcc    1620
cgtatggcct caatctccca atcggcccga ggatcagagg ataagagact ctctctcttc    1680
gttttccctg caggccccat cggctcatgg acacccgcac tcgcggccgg cgacgccacc    1740
ccacgctccc ttttcaaacg gcgcgagcgg agggtcggat acctttggca gctggtcgtg    1800
gggcgcggca tcgaaccgcg agagcaagac gattggagcg ttgaaggagt cgtcagcgcc    1860
gcccaccagg aggggcagca tggcacacat cctcaacccc agcgataccg ctgagcgatc    1920
agacgaggac gaggaccccc ggggcgacga cgacagaaag cgaaaacgaa gacag        1975

<210> SEQ ID NO 2
<211> LENGTH: 1900
<212> TYPE: DNA
<213> ORGANISM: Trichoderma reesei

<400> SEQUENCE: 2
atgggccaag ccccttctca gacgcggcgg actcggcgga cgcacgagga actgacacag      60
gagcttgtga gcgcgccgtt gcaccttggc ctgggaacaa gcaagggcct aggctttgct     120
aactgtgcgt gaacaggcgt acagattcaa ggaaaagtgc ttcacgtcgc tggagtacta     180
ctcactgaag gatgtcttca agaaactggc cgaccagcag ggcgacatac ggtatctcaa     240
ggaggacacc atagctcgct cctcgagat cccagacatc ctcggggctt cgccggtcat      300
cttccacatg atctcgtatc tgggtgcgtt tccctttctg caggaggccc ccgtggtgct     360
cgagctggcg cagttgatca tggtcgttgt catcatgacg gagcgatata agcgcgttct     420
tgcgaagggc tcgacagaca ggacgaaatt attttttaaa agcttggctg tgtatgaccg     480
gaaagtgatg gaggagaccg gttcttcacc gcggaattcc acttcaaaag acgccactgc     540
gaggccgagc gccaacacaa gaggctttgc aatcgacgag ccgatggccg aggacgagga     600
tgatggcgac gacgacgacg atgatcttgt cattacggcc ttcgagctgc tcgacatcga     660
tgaagctacc aagcacggag aagccgctgc cattaaagaa gccatcatcc cgaccgacaa     720
cttccgcaaa cttattatgc tgctgctgct gattgcgcca ctggatgctc aggagagtct     780
atcgcaatat ccagccgggt cgcgggccc cgaactagag tcgctgcgag ccacggcaga      840
gtgtgtacta gcatccttcg tcgatgtcga gacgtcgcca ggcattggat atacccggtt     900
caagactgtc attccggtcc tattccccaa cctctttgct gggttcaatg gcctgtttga     960
acactttctt ttctccaagg atctggactt ctcgaagcac aaggttgaga gcctggtga    1020 cgagcagctc atcattggca agattgcgca acctctgctc ccaaccctg gcgacatcat    1080 gactgagcat acgctgtcgc aactttcact gtttctacct ggctcctctc tgttccgaag    1140
agtgagattg ctctattcgg gaaacgatgc tggattctcc atgggcagcc tccagaccaa    1200
ggtctttaac tggagagccc caaccattct tctagtcagc ggatcgagat tagcagacgt    1260
ccccgaggga ggccaagagg catcgttcgc ctcttcgctt ccaccaaac ggttccctca    1320 tggtagtaaa tccgagcgtg taacgtttgg cgtgtacgtt cgagagcctt ggaagcacac    1380
gcacaaagag tgcttcggca attcggaaac aatactcttt caactagaac ccattcacga    1440
tgttttccct gcctctacaa tcaatacaga ctacgtcacc ttcacgaaac cacctggcaa    1500
```

| | |
|---|---|
| ccggccctgt ctagcatttg ggtgcccaca ccccaaaccg acgcagtcgc atcgcaagga | 1560 |
| gggcatacat gctttaggag ccgtgtctct gttgtttgat gaatctttcg agttcggagt | 1620 |
| cttcaatcat gactacaagt cgagagggggg cgctttccac actagcatcg tgaggaaata | 1680 |
| tgattttcag gatcggtttc gaatcggaaa catggaagtc tggggatgtg gtggtgacga | 1740 |
| ggaggccaag gcgcaagcag agagatgggc ttgggaagaa cgtgaagcgg aagcccgtcg | 1800 |
| caggatcaac cttgggacgg gtgacattga ggcggacagg gcattgctgg agatggccgg | 1860 |
| gctagtagga gggaatcgca gcggcggttc aatgggttga | 1900 |

<210> SEQ ID NO 3
<211> LENGTH: 3545
<212> TYPE: DNA
<213> ORGANISM: Trichoderma reesei

<400> SEQUENCE: 3

| | |
|---|---|
| atgacccaag agcctctcaa gactccagca cagctcccgg ccaacaatca tctcgattcc | 60 |
| ctccaactcc cccagcatgg ctcccttcat cgcgacgcca gtgggccctgg tcgaggcctt | 120 |
| cccggcttca gcctcggctc gcagcgcctt cgcctcgacc cggctgagca tcagggccgg | 180 |
| gaagccggag tgaacgctga acggctggac gagaagctgc aacaattgag cctcgatgga | 240 |
| gcccacgacg gtcgcccttc tgtgcccgga cagcgagtct acgagtatga gaaggcctcg | 300 |
| actccccaag cctctaagca gggccttgga ttccaggtca tcaaacgctc agagccccac | 360 |
| gccgatggac tcagtctcga ggactttccc aatggttggt tctgcctctt ccttgcggcg | 420 |
| agcgaccat tgctgaccaa tgactgccag agatcctcac ccacatcttt tctcatctgc | 480 |
| cccccgactg ccactcgtcg gtggcgctgg tctcgaagcg attctgggcg ctggtcacca | 540 |
| cccatcatgc gtggcgcatg gccttttatgc gcttcttccc gggacacacc atcctggaga | 600 |
| acaacggcaa ggctgccgcc gccactcatt ccatgactgg gccatcctcc gacgttgtgc | 660 |
| gttcgagac gcgatacttc cctcgactca cgccgctggc cacttggagg agcgagtatc | 720 |
| ttctacggac tcgccaccta gaagcttgg ctcgcggcaa accagggcct cccgccggtg | 780 |
| ggagtgtgtc tggccgcgtc ggtcgcgtg ggaagaagtc aagcgccgtc ttgacctaca | 840 |
| actcgaaact gccttggcag gtgacgaatc tccacgccgt cttcctgaat ggaaagaaac | 900 |
| cgccccgcgt tatgcaaggc gccggagatc tcggtgcggc aaccattagc gaccccacga | 960 |
| ctggaaagat tgagaaatgg ggcattgagg atctatacac cactcctcag ctggacgagg | 1020 |
| ttgcccccaa cctggtgcct tacgcttgg gagacgcccc agccggcgtc cccaatgtca | 1080 |
| tggatgtgag ctacacgtac ggcatgatat ctggggaggg atttccaggt ggccggccct | 1140 |
| actttcgagg ggtcaatgaa atgcgtggtc gctacgttgg cgcagagatc agtgccgtcg | 1200 |
| acactcatcc ggatattccc aagattcccg aaatgtccga tgcgatctgc agcgtctgga | 1260 |
| ttgccaagtc atcgaccgtc acggcgacga ctcaatccat gtgcggcatg ctcacaggct | 1320 |
| ctgctctcgg tattatcacg gcctattcac ttggctggga taccacgggc ccgagatatg | 1380 |
| ccaatggcga cgtcaccgca cgatgggtcg ttagccctgg tgttcccatc atatccctca | 1440 |
| aggtcgatga tggcttcaac cagaagcgca agtcgtcctc cagggtatgg gcggtggctt | 1500 |
| tgaacgccct cggtgaggtt tactacctgt gcgatgtacc cgttggcaaa cccgggcgaa | 1560 |
| ctactgcgca ggacatgacg aggaatgcct ggtatgctgg ccgtacagcc tactggcacc | 1620 |
| ttctcgaggc gactcgcaga gttgctcgtg aagacgaggc tgacaaaaac gcaactcgtg | 1680 |
| gaggctattc gcctcgatcg ccttctctcg acatgcatct cagcaaggaa cagattgtgg | 1740 |

-continued

```
cagaggctcg ggagattgaa aagtttatgc gctatcggcc ctcccacttt cgaaaggtct    1800
gcgagggctg ggacatgcag cggaagctgg aggtcgactt tgcgagtgat gatgggaaag    1860
gtgccggcga gagcatcttt gtcatcgatt gcggcctggc agagaaccgc cctgttagca    1920
tccagcgcta ttcgcgttca ttgatacccg ttcaggcac tccagcgaa tcctcgacac      1980 cacttgcgcc ggtcccgaca tcgctgtttg gcagcatcgg aggctttgcc aaccgcattt    2040
ctcctgtttc tgaatcccaa cgccattgt ctccgccacc tactcctaaa tcgcccctg      2100 tgccttcgac ggttcttcat gactggttca acaagggtt cgagttcaag ggccacggtc     2160
acgataccat attgtcagtt gctttggaca attcgctcac ctcgctctac acacttgggg    2220
aggaccctct acacaccgcg aacgaagcgt cctccacgac gagcccctgg gctgaacacg    2280
gggcgaggga gattcctggg cgccgaaccc gcttcatcat cgctggaacc aactccggcg    2340
cggtgcttgt ctggaatgcg cgtgatgacg atcgaactcg tgatatacaa ccactgcgca    2400
tccttcagac cgagtcacca gaggtttctg ctgtggcagc ctctgggttg tatctcgttc    2460
acggcggcag cgacggcctt gtccaagcct gggatccctt ggcatctaca acggatccca    2520
tcagaacgat taacgctcgg tcaaatggcc gggtccccg tcacatgctg gtaatgaatc     2580
ccgcattgca ggaggagaca tactcggcag caaaggccat atatcttgac cctgattcta    2640
cgacgcttca aggtgtagtc tcttttggcg cattcctgcg atattggtcg tatgggtcca    2700
atggtcatgc cacaggtcgc aagcggcgcg tccgacacgc cgatatggac gctcggcttg    2760
cgagtcgccg gcaaggccat gcagtgtcag gctacattgc ctctgaggaa gccgagatgc    2820
gacgggagga tgagcagcag gctcgcgagc acaaccgtcg tctcaagaga tttggcgctc    2880
taggcgactt gaccgaggaa gaagcgcttc tctacgccca gatggtctcc caagaggcgt    2940
accacgtaga ggagcagcga cgggccagcg attcggcagc cgacgccagc ctggacaccg    3000
cctcttcctt tagcgagaat accgtcgaga ctctgacacc tgatccgagc gtcgccgatc    3060
cggtcgcttc ggaaacgagc ggcatggccg aggatgacga gtacgagcag cagattcagc    3120
aggctatacg tctgtctctg ctagaaggcg tcaacaacgg cgtggaacag tcacctgtgg    3180
attcctcacg gggcaacagc tctgttgatt tcgaccaacc ggtcaatgtc aagtacaagc    3240
ccaagggcgg gaagaagggg aagcaatcag gggcttcttc tggtggctca ccgtctgcga    3300
gccacacgcc cgttggtggt ggtgcttctt cttcgcggct gagcacgact gaagatgagg    3360
atttagcgat tgctctgagt ctgagcatgc aggaccaggg aggggatac tcgccgccgg     3420 gaatgtcgtc gtcgacgatg atggggagga gtgcttactt ggaggctgct gctggtgtcg    3480
atgaggagga tgagtttccg tctttgcctg gtgaagggaa ggggaagggg gtgcagagat    3540
ggtga                                                                3545
```

<210> SEQ ID NO 4
<211> LENGTH: 553
<212> TYPE: PRT
<213> ORGANISM: Trichoderma reesei

<400> SEQUENCE: 4

```
Pro Thr Ile Ser Met Ser Pro Ser Pro Val Asp His Pro Met Glu
1               5                   10                  15

Gly Thr Ser Pro Glu Asp Asn Ser Pro Thr Gly His Gly His Gly Ser
            20                  25                  30

Gly Ser Asp Pro Glu Gly Ser Ser Asn Gly Lys Pro Pro Val Ser Arg
        35                  40                  45
```

-continued

Ala Gly Asn Ala Ser Pro Gln Glu His Gly Ala Leu Thr Thr Ser Ser
        50                  55                  60

Asn Met Pro Ala Pro Pro Ala Ala Ala Ala Val His Gln Pro
65                  70                  75                  80

Lys Ile Val Gln Thr Ala Phe Ile His Lys Leu Tyr Asn Met Leu Glu
                        85                  90                  95

Asp Thr Ser Ile Gln His Leu Ile Ser Trp Ser Ser Ala Glu Ser
                100                 105                 110

Phe Val Met Ser Pro Ser Ala Asp Phe Ser Lys Val Leu Ser Gln Tyr
            115                 120                 125

Phe Lys His Thr Asn Ile Ser Ser Phe Val Arg Gln Leu Asn Met Tyr
        130                 135                 140

Gly Phe His Lys Glu Arg Asp Val Phe His Thr Gly Asn Pro Glu Thr
145                 150                 155                 160

Thr Leu Trp Glu Phe Lys His Gly Asn Gly Asn Phe Lys Arg Gly Asp
                165                 170                 175

Leu Val Gly Leu Arg Glu Ile Lys Arg Arg Ala Ser Arg His Ala Leu
            180                 185                 190

Val Asn Arg Glu Asn Thr Phe Pro Lys Thr Ser Thr Ser Gln Pro Gly
        195                 200                 205

Thr Pro Ile Glu Pro Val Gln Val Pro Pro Asp Ser Ile Glu Ala Arg
210                 215                 220

Ile Ala Asn Leu Glu His Ser Leu Tyr Asp Thr Ala Ala Arg Leu Gln
225                 230                 235                 240

Arg Ser Glu Glu Ser Ala His Tyr Met His Val Lys Asn Gln Ala Ile
                245                 250                 255

Met Glu Thr Leu Asn Arg Leu Leu Phe Phe Asn Gln Glu Leu Ser Lys
            260                 265                 270

Gly Ile Leu Ser Leu Val Pro Pro Asp Asn Pro Val His Arg Asp Val
        275                 280                 285

Met Thr Leu Gln Gly Glu Met Val Arg Gln Ala Glu Met Leu Arg Ser
290                 295                 300

Leu Asp Glu Pro His Glu Pro Val Tyr Ser Ala Arg Gln Gln Phe Phe
305                 310                 315                 320

Gly Thr Val Asp Asn Ala Pro Val Ser Pro Arg Gln Leu Pro Gln Asp
                325                 330                 335

Asp Asn Arg Arg Val Thr Leu Asn Val Pro Gln Gly Arg Ser Gln Pro
            340                 345                 350

Ser Tyr Arg Pro Ala Val Pro Ser Asn Leu Ser Ala Gly Thr Arg Arg
        355                 360                 365

Pro Tyr Gly Ser Ile Ser Gly Gly Ala Gly Ser Ser Pro Leu Arg Asn
370                 375                 380

Ala Ala Pro Ala Pro Pro Ala Gly Pro His Pro Leu Ser Asn Val Glu
385                 390                 395                 400

Thr Val Pro Ser Asn Leu Ala Arg Arg His Thr Ala Ala Asp Ile Arg
                405                 410                 415

Ala His Gly Trp Gln Pro Asn Ala Pro Pro Tyr Pro Pro Gly Ala Val
            420                 425                 430

Pro Pro Pro Val Trp Pro Gln Ser Pro Asn Arg Pro Glu Asp Gln Arg
        435                 440                 445

Ile Arg Asp Ser Leu Ser Ser Phe Ser Leu Gln Ala Pro Ser Ala His
450                 455                 460

```
Gly His Pro His Ser Arg Pro Ala Thr Pro His Ala Pro Phe Ser
465                 470                 475                 480

Asn Gly Ala Ser Gly Ser Asp Thr Phe Gly Ser Trp Ser Trp Gly
            485                 490                 495

Ala Ala Ser Asn Arg Glu Ser Lys Thr Ile Gly Ala Leu Lys Glu Ser
            500                 505                 510

Ser Ala Pro Pro Thr Arg Arg Gly Ser Met Ala His Ile Leu Asn Pro
            515                 520                 525

Ser Asp Thr Ala Glu Arg Ser Asp Glu Asp Glu Asp Pro Arg Gly Asp
            530                 535                 540

Asp Asp Arg Lys Arg Lys Arg Gln
545                 550
```

<210> SEQ ID NO 5
<211> LENGTH: 609
<212> TYPE: PRT
<213> ORGANISM: Trichoderma reesei

<400> SEQUENCE: 5

```
Met Gly Gln Ala Pro Ser Gln Thr Arg Arg Thr Arg Arg Thr His Glu
1               5                   10                  15

Glu Leu Thr Gln Glu Leu Ala Tyr Arg Phe Lys Glu Lys Cys Phe Thr
            20                  25                  30

Ser Leu Glu Tyr Tyr Ser Leu Lys Asp Val Phe Lys Lys Leu Ala Asp
            35                  40                  45

Gln Gln Gly Asp Ile Arg Tyr Leu Lys Glu Asp Thr Ile Ala Arg Phe
        50                  55                  60

Leu Glu Ile Pro Asp Ile Leu Gly Ala Ser Pro Val Ile Phe His Met
65                  70                  75                  80

Ile Ser Tyr Leu Gly Ala Phe Pro Phe Leu Gln Glu Ala Pro Val Val
                85                  90                  95

Leu Glu Leu Ala Gln Leu Ile Met Val Val Ile Met Thr Glu Arg
            100                 105                 110

Tyr Lys Arg Val Leu Ala Lys Gly Ser Thr Asp Arg Thr Lys Leu Phe
            115                 120                 125

Phe Lys Ser Leu Ala Val Tyr Asp Arg Lys Val Met Glu Glu Thr Gly
        130                 135                 140

Ser Ser Pro Arg Asn Ser Thr Ser Lys Asp Ala Thr Ala Arg Pro Ser
145                 150                 155                 160

Ala Asn Thr Arg Gly Phe Ala Ile Asp Glu Pro Met Ala Glu Asp Glu
                165                 170                 175

Asp Asp Gly Asp Asp Asp Asp Asp Leu Val Ile Thr Ala Phe Glu
            180                 185                 190

Leu Leu Asp Ile Asp Glu Ala Thr Lys His Gly Glu Ala Ala Ala Ile
            195                 200                 205

Lys Glu Ala Ile Ile Pro Thr Asp Asn Phe Arg Lys Leu Ile Met Leu
        210                 215                 220

Leu Leu Leu Ile Ala Pro Leu Asp Ala Gln Glu Ser Leu Ser Gln Tyr
225                 230                 235                 240

Ser Ser Arg Val Ala Gly Pro Glu Leu Glu Ser Leu Arg Ala Thr Ala
                245                 250                 255

Glu Cys Val Leu Ala Ser Phe Val Asp Val Glu Thr Ser Pro Gly Ile
            260                 265                 270

Gly Tyr Thr Arg Phe Lys Thr Val Ile Pro Val Leu Phe Pro Asn Leu
            275                 280                 285
```

```
Phe Ala Gly Phe Asn Gly Leu Phe Glu His Phe Leu Phe Ser Lys Asp
            290                 295                 300

Leu Asp Phe Ser Lys His Lys Val Glu Lys Pro Gly Asp Glu Gln Leu
305                 310                 315                 320

Ile Ile Gly Lys Ile Ala Gln Pro Leu Pro Thr Pro Gly Asp Ile
                325                 330                 335

Met Thr Glu His Thr Leu Ser Gln Leu Ser Leu Phe Leu Pro Gly Ser
            340                 345                 350

Ser Leu Phe Arg Arg Val Arg Leu Leu Tyr Ser Gly Asn Asp Ala Gly
            355                 360                 365

Phe Ser Met Gly Ser Leu Gln Thr Lys Val Phe Asn Trp Arg Ala Pro
370                 375                 380

Thr Ile Leu Leu Val Ser Gly Ser Arg Leu Ala Asp Val Pro Glu Gly
385                 390                 395                 400

Gly Gln Glu Ala Ser Phe Ala Ser Ser Leu Pro Thr Lys Arg Phe Pro
                405                 410                 415

His Gly Ser Lys Ser Glu Arg Val Thr Phe Gly Val Tyr Val Arg Glu
            420                 425                 430

Pro Trp Lys His Thr His Lys Glu Cys Phe Gly Asn Ser Glu Thr Ile
                435                 440                 445

Leu Phe Gln Leu Glu Pro Ile His Asp Val Phe Pro Ala Ser Thr Ile
450                 455                 460

Asn Thr Asp Tyr Val Thr Phe Thr Lys Pro Pro Gly Asn Arg Pro Cys
465                 470                 475                 480

Leu Ala Phe Gly Cys Pro His Pro Lys Pro Thr Gln Ser His Arg Lys
                485                 490                 495

Glu Gly Ile His Ala Leu Gly Ala Val Ser Leu Leu Phe Asp Glu Ser
            500                 505                 510

Phe Glu Phe Gly Val Phe Asn His Asp Tyr Lys Ser Arg Gly Gly Ala
            515                 520                 525

Phe His Thr Ser Ile Val Arg Lys Tyr Asp Phe Gln Asp Arg Phe Arg
            530                 535                 540

Ile Glu Asn Met Glu Val Trp Gly Cys Gly Gly Asp Glu Glu Ala Lys
545                 550                 555                 560

Ala Gln Ala Glu Arg Trp Ala Trp Glu Glu Arg Glu Ala Glu Ala Arg
                565                 570                 575

Arg Arg Ile Asn Leu Gly Thr Gly Asp Ile Glu Ala Asp Arg Ala Leu
                580                 585                 590

Leu Glu Met Ala Gly Leu Val Gly Gly Asn Arg Ser Gly Gly Ser Met
            595                 600                 605

Gly

<210> SEQ ID NO 6
<211> LENGTH: 1162
<212> TYPE: PRT
<213> ORGANISM: Trichoderma reesei

<400> SEQUENCE: 6

Met Thr Gln Glu Pro Leu Lys Thr Pro Ala Gln Leu Pro Ala Asn Asn
1               5                   10                  15

His Leu Asp Ser Leu Gln Leu Pro Gln His Gly Ser Leu His Arg Asp
            20                  25                  30

Ala Ser Gly Pro Gly Arg Gly Leu Pro Gly Phe Ser Leu Gly Ser Gln
        35                  40                  45
```

-continued

Arg Leu Arg Leu Asp Pro Ala Glu His Gln Gly Arg Glu Ala Gly Val
    50              55                  60

Asn Ala Glu Arg Leu Asp Glu Lys Leu Gln Gln Leu Ser Leu Asp Gly
65                  70                  75                  80

Ala His Asp Gly Arg Pro Ser Val Pro Gly Gln Arg Val Tyr Glu Tyr
                    85                  90                  95

Glu Lys Ala Ser Thr Pro Gln Ala Ser Lys Gln Gly Leu Gly Phe Gln
                100                 105                 110

Val Ile Lys Arg Ser Glu Pro His Ala Asp Gly Leu Ser Leu Glu Asp
            115                 120                 125

Phe Pro Asn Glu Ile Leu Thr His Ile Phe Ser His Leu Pro Pro Asp
    130                 135                 140

Cys His Ser Ser Val Ala Leu Val Ser Lys Arg Phe Trp Ala Leu Val
145                 150                 155                 160

Thr Thr His His Ala Trp Arg Met Ala Phe Met Arg Phe Phe Pro Gly
                    165                 170                 175

His Thr Ile Leu Glu Asn Asn Gly Lys Ala Ala Ala Thr His Ser
                180                 185                 190

Met Thr Gly Pro Ser Ser Asp Val Val Arg Phe Glu Thr Arg Tyr Phe
    195                 200                 205

Pro Arg Leu Thr Pro Leu Ala Thr Trp Arg Ser Glu Tyr Leu Leu Arg
    210                 215                 220

Thr Arg His Leu Arg Ser Leu Ala Arg Gly Lys Pro Gly Pro Pro Ala
225                 230                 235                 240

Gly Gly Ser Val Ser Gly Arg Val Gly Gly Lys Lys Ser Ser
                    245                 250                 255

Ala Val Leu Thr Tyr Asn Ser Lys Leu Pro Trp Gln Val Thr Asn Leu
                260                 265                 270

His Ala Val Phe Leu Asn Gly Lys Lys Pro Pro Arg Val Met Gln Gly
            275                 280                 285

Ala Gly Asp Leu Gly Ala Ala Thr Ile Ser Asp Pro Thr Thr Gly Lys
    290                 295                 300

Ile Glu Lys Trp Gly Ile Glu Asp Leu Tyr Thr Thr Pro Gln Leu Asp
305                 310                 315                 320

Glu Val Ala Pro Asn Leu Val Pro Tyr Gly Leu Gly Asp Gly Pro Ala
                325                 330                 335

Gly Val Pro Asn Val Met Asp Val Ser Tyr Thr Tyr Gly Met Ile Ser
                340                 345                 350

Gly Glu Gly Phe Pro Gly Gly Arg Pro Tyr Phe Arg Gly Val Asn Glu
            355                 360                 365

Met Arg Gly Arg Tyr Val Gly Ala Glu Ile Ser Ala Val Asp Thr His
    370                 375                 380

Pro Asp Ile Pro Lys Ile Pro Glu Met Ser Asp Ala Ile Cys Ser Val
385                 390                 395                 400

Trp Ile Ala Lys Ser Ser Thr Val Thr Ala Thr Thr Gln Ser Met Cys
                405                 410                 415

Gly Met Leu Thr Gly Ser Ala Leu Gly Ile Ile Thr Ala Tyr Ser Leu
                420                 425                 430

Gly Trp Asp Thr Thr Gly Pro Arg Tyr Ala Asn Gly Asp Val Thr Ala
            435                 440                 445

Arg Trp Val Val Ser Pro Gly Val Pro Ile Ile Ser Leu Lys Val Asp
    450                 455                 460

-continued

```
Asp Gly Phe Asn Gln Lys Arg Lys Ser Ser Ser Arg Val Trp Ala Val
465                 470                 475                 480

Ala Leu Asn Ala Leu Gly Glu Val Tyr Tyr Leu Cys Asp Val Pro Val
                485                 490                 495

Gly Lys Pro Gly Arg Thr Thr Gly Glu Asp Met Thr Arg Asn Ala Trp
            500                 505                 510

Tyr Ala Gly Arg Thr Ala Tyr Trp His Leu Leu Glu Ala Thr Arg Arg
        515                 520                 525

Val Ala Arg Glu Asp Glu Ala Asp Lys Asn Ala Thr Arg Gly Gly Tyr
    530                 535                 540

Ser Pro Arg Ser Pro Ser Leu Asp Met His Leu Ser Lys Glu Gln Ile
545                 550                 555                 560

Val Ala Glu Ala Arg Glu Ile Glu Lys Phe Met Arg Tyr Arg Pro Ser
                565                 570                 575

His Phe Arg Lys Val Cys Glu Gly Trp Asp Met Gln Arg Lys Leu Glu
            580                 585                 590

Val Asp Phe Ala Ser Asp Asp Gly Lys Gly Ala Gly Glu Ser Ile Phe
        595                 600                 605

Val Ile Asp Cys Gly Leu Ala Glu Asn Arg Pro Val Ser Ile Gln Arg
    610                 615                 620

Tyr Ser Arg Ser Leu Ile Pro Val Gln Gly Thr Pro Ser Glu Ser Ser
625                 630                 635                 640

Thr Pro Leu Ala Pro Val Pro Thr Ser Leu Phe Gly Ser Ile Gly Gly
                645                 650                 655

Phe Ala Asn Arg Ile Ser Pro Val Ser Glu Ser Gln Ala Pro Leu Ser
            660                 665                 670

Pro Pro Pro Thr Pro Lys Ser Pro Pro Val Pro Ser Thr Val Leu His
        675                 680                 685

Asp Trp Phe Lys Gln Gly Phe Glu Phe Lys Gly His Gly His Asp Thr
    690                 695                 700

Ile Leu Ser Val Ala Leu Asp Asn Ser Leu Thr Ser Leu Tyr Thr Leu
705                 710                 715                 720

Gly Glu Asp Pro Leu His Thr Ala Asn Glu Ala Ser Ser Thr Thr Ser
                725                 730                 735

Pro Trp Ala Glu His Gly Ala Arg Glu Ile Pro Gly Arg Arg Thr Arg
            740                 745                 750

Phe Ile Ile Ala Gly Thr Asn Ser Gly Ala Val Leu Val Trp Asn Ala
        755                 760                 765

Arg Asp Asp Asp Arg Thr Arg Asp Ile Gln Pro Leu Arg Ile Leu Gln
    770                 775                 780

Thr Glu Ser Pro Glu Val Ser Ala Val Ala Ala Ser Gly Leu Tyr Leu
785                 790                 795                 800

Val His Gly Gly Ser Asp Gly Leu Val Gln Ala Trp Asp Pro Leu Ala
                805                 810                 815

Ser Thr Thr Asp Pro Ile Arg Thr Ile Asn Ala Arg Ser Asn Gly Arg
            820                 825                 830

Val Pro Arg His Met Leu Val Met Asn Pro Ala Leu Gln Glu Glu Thr
        835                 840                 845

Tyr Ser Ala Ala Lys Ala Ile Tyr Leu Asp Pro Asp Ser Thr Thr Leu
    850                 855                 860

Gln Gly Val Val Ser Phe Gly Ala Phe Leu Arg Tyr Trp Ser Tyr Gly
865                 870                 875                 880

Ser Asn Gly His Ala Thr Gly Arg Lys Arg Arg Val Arg His Ala Asp
```

```
              885                 890                 895
Met Asp Ala Arg Leu Ala Ser Arg Arg Gln Gly His Ala Val Ser Gly
            900                 905                 910

Tyr Ile Ala Ser Glu Glu Ala Glu Met Arg Arg Glu Asp Glu Gln Gln
            915                 920                 925

Ala Arg Glu His Asn Arg Arg Leu Lys Arg Phe Gly Ala Leu Gly Asp
            930                 935                 940

Leu Thr Glu Glu Ala Leu Leu Tyr Ala Gln Met Val Ser Gln Glu
945                 950                 955                 960

Ala Tyr His Val Glu Glu Gln Arg Arg Ala Ser Asp Ser Ala Ala Asp
            965                 970                 975

Ala Ser Leu Asp Thr Ala Ser Ser Phe Ser Glu Asn Thr Val Glu Thr
            980                 985                 990

Leu Thr Pro Asp Pro Ser Val Ala Asp Pro Val Ala Ser Glu Thr Ser
            995                 1000                1005

Gly Met Ala Glu Asp Asp Glu Tyr Glu Gln Gln Ile Gln Gln Ala
        1010                1015                1020

Ile Arg Leu Ser Leu Leu Glu Gly Val Asn Asn Gly Val Glu Gln
        1025                1030                1035

Ser Pro Val Asp Ser Ser Arg Gly Asn Ser Ser Val Asp Phe Asp
        1040                1045                1050

Gln Pro Val Asn Val Lys Tyr Lys Pro Lys Gly Gly Lys Lys Gly
        1055                1060                1065

Lys Gln Ser Gly Ala Ser Ser Gly Gly Ser Pro Ser Ala Ser His
        1070                1075                1080

Thr Pro Val Gly Gly Gly Ala Ser Ser Ser Arg Leu Ser Thr Thr
        1085                1090                1095

Glu Asp Glu Asp Leu Ala Ile Ala Leu Ser Leu Ser Met Gln Asp
        1100                1105                1110

Gln Gly Gly Gly Tyr Ser Pro Pro Gly Met Ser Ser Thr Met
        1115                1120                1125

Met Gly Arg Ser Ala Tyr Leu Glu Ala Ala Ala Gly Val Asp Glu
        1130                1135                1140

Glu Asp Glu Phe Pro Ser Leu Pro Gly Glu Gly Lys Gly Lys Gly
        1145                1150                1155

Val Gln Arg Trp
        1160

<210> SEQ ID NO 7
<211> LENGTH: 859
<212> TYPE: PRT
<213> ORGANISM: Trichoderma reesei

<400> SEQUENCE: 7

Met Pro His Arg Glu Arg Gly Lys Gln Arg Glu Gly Gly Asp Ser Tyr
1               5                   10                  15

Arg Pro Ser Arg Pro Ala Arg Ser Ser Arg Ser Ser Pro Pro
            20                  25                  30

Arg Ala Pro Val Pro Val Arg Thr Glu Glu Lys Gln Ala Ala Ala
        35                  40                  45

Lys Ala Glu Tyr Glu Lys Leu Leu Asn Met Arg Ser Gly Gly Thr Tyr
    50                  55                  60

Ile Pro Pro Ala Arg Leu Arg Ala Leu Gln Ala Gln Ile Thr Asp Lys
65                  70                  75                  80
```

Ser Ser Lys Glu Tyr Gln Arg Met Ala Trp Glu Ala Leu Lys Lys Ser
            85                  90                  95

Ile Asn Gly Leu Ile Asn Lys Val Asn Thr Ala Asn Ile Lys His Ile
            100                 105                 110

Val Pro Glu Leu Phe Gly Glu Asn Leu Val Arg Gly Arg Gly Leu Phe
            115                 120                 125

Cys Arg Ser Ile Met Lys Ala Gln Ala Ala Ser Leu Pro Phe Thr Pro
130                 135                 140

Ile Tyr Ala Ala Met Ala Ala Ile Val Asn Thr Lys Leu Pro Gln Val
145                 150                 155                 160

Gly Glu Leu Leu Val Lys Arg Leu Ile Met Gln Phe Arg Lys Gly Phe
                    165                 170                 175

Lys Arg Asn Asp Lys Ala Val Cys Leu Ser Ser Thr Thr Phe Leu Ala
                    180                 185                 190

His Leu Ile Asn Gln Gln Val Gln His Glu Met Leu Ala Gly Gln Ile
            195                 200                 205

Leu Leu Leu Leu Leu His Lys Pro Thr Asp Asp Ser Val Glu Ile Ala
            210                 215                 220

Val Gly Phe Cys Lys Glu Val Gly Gln Tyr Leu Glu Glu Met Gln Pro
225                 230                 235                 240

Ala Ile Ser Met Ala Val Phe Asp Gln Phe Arg Asn Ile Leu His Glu
                    245                 250                 255

Ser Asp Ile Asp Lys Arg Thr Gln Tyr Met Ile Glu Val Leu Phe Gln
                    260                 265                 270

Ile Arg Lys Asp Lys Phe Lys Asp His Pro Ala Ile Lys Glu Glu Leu
                    275                 280                 285

Asp Leu Val Glu Glu Glu Asp Gln Ile Thr His Lys Val Glu Leu Asp
            290                 295                 300

Gly Glu Ile Asp Val Gln Asp Gly Leu Asn Ile Phe Lys Tyr Asp Pro
305                 310                 315                 320

Glu Trp Glu Glu His Glu Glu Ala Tyr Lys Arg Leu Lys Ala Glu Ile
                    325                 330                 335

Leu Gly Glu Ala Ser Asp Asp Glu Glu Gly Asp Glu Asp Glu Asp Glu
                    340                 345                 350

Asp Glu Ser Ser Glu Asp Glu Glu Asn Glu Glu Thr Lys Ala Met Glu
            355                 360                 365

Ile Lys Asp Gln Ser Asn Ala Asp Leu Val Asn Leu Arg Arg Thr Ile
            370                 375                 380

Tyr Leu Thr Ile Met Ser Ser Ala Asp Pro Glu Glu Ala Val His Lys
385                 390                 395                 400

Leu Met Lys Ile Asn Leu Pro Val Gly Gln Glu Pro Glu Leu Pro Ser
                    405                 410                 415

Met Ile Val Glu Cys Cys Ser Gln Glu Lys Thr Tyr Thr Lys Phe Phe
                    420                 425                 430

Gly Leu Ile Gly Glu Arg Phe Ala Lys Ile Asn Arg Leu Trp Cys Asp
            435                 440                 445

Leu Phe Glu Gln Ala Phe Val Lys Tyr Tyr Gly Thr Ile His Arg Tyr
            450                 455                 460

Glu Asn Asn Lys Leu Arg Asn Ile Ala Met Leu Phe Gly His Met Phe
465                 470                 475                 480

Ala Ser Asp Ala Leu Gly Trp His Cys Leu Ser Val Ile His Leu Asn
                    485                 490                 495

Glu Glu Glu Thr Thr Ser Ser Ser Arg Ile Phe Ile Lys Ile Leu Phe 500                 505                 510
    Gln His Ile Ser Glu Glu Ile Gly Leu Ala Lys Leu Arg Ala Arg Met
                515                 520                 525

Thr Asp Glu Thr Leu Arg Pro Ser Leu Glu Gly Leu Phe Pro Arg Glu
    530                 535                 540

Asn Pro Arg Asn Ile Arg Phe Ser Ile Asn Tyr Phe Thr Ser Ile Gly
    545                 550                 555                 560

Met Gly Val Leu Thr Glu Glu Met Arg Glu His Leu Met Asn Met Pro
                    565                 570                 575

Lys Pro Ala Leu Pro Ala Pro Ala Ala Gln Asp Arg Ser Asp Thr Asp
                580                 585                 590

Ser Val Ser Ser Tyr Ser Ser Tyr Thr His Ser Ser Tyr Ser Ser Arg
                595                 600                 605

Ser Arg Ser Arg Ser Arg Ser Val Gly Arg Arg Ser Gly Gly Arg Gly
                610                 615                 620

Arg Ser Leu Ser Arg Thr Pro Pro Arg Gly Ala Arg Ser Arg Ser
    625                 630                 635                 640

Tyr Ser Asp Asp Ser Arg Ser Pro Ser Arg Ser Arg Ser Arg Ser Arg
                    645                 650                 655

Ser Asp Ser Val Ser Thr Arg Gly Arg Arg Ala Ser Tyr Ser Ala
                    660                 665                 670

Ser Pro Pro Arg Gly Gly Arg Arg Val Ala Ser Arg Ser Arg Ser
                    675                 680                 685

Tyr Ser Ser Gly Ser Ser Arg Ser Pro Pro Arg Asn Arg Gly Arg
                    690                 695                 700

Ala Arg Ser Asn Ser Tyr Ser Ser Tyr Ser Arg Ser Pro Ser Ser
    705                 710                 715                 720

Pro Arg Arg Gly Arg Asp Ala Asp Ser Ala Ser Pro Pro Arg Arg
                    725                 730                 735

Gly Arg Pro Arg Gln Ser Pro Gly Gly Pro Ala Gly Arg Arg Asn
                    740                 745                 750

Ser Ser Ser Val Gly Ser Gly Gly Pro Arg Lys Lys Pro Arg Arg Asp
                755                 760                 765

Ser Arg Ser Pro Ser Arg Asp Tyr Ser Ser Arg Ser Pro Ser Arg Ser
    770                 775                 780

Pro Ser Arg Ser Arg Ser Pro Pro Ala Ala Arg Gly Arg Arg Gly
    785                 790                 795                 800

Ser Tyr Thr Pro Ser Arg Ser Arg Ser Pro Pro Arg Arg Val Arg
                    805                 810                 815

Asp Gly Ser Pro Gly Arg Leu Arg Gly Gly Arg Ser Pro Ser Pro Pro
                820                 825                 830

Leu Pro Val Lys Arg Arg Tyr Asp Ser Glu Ser Val Ser Arg Ser
                835                 840                 845

Pro Pro Pro Leu Lys Arg Gly Arg Arg Asp Asn
        850                 855

<210> SEQ ID NO 8
<211> LENGTH: 2580
<212> TYPE: DNA
<213> ORGANISM: Trichoderma reesei

<400> SEQUENCE: 8
atgccgcacc gcgagcgcgg caagcagcga gaaggcggcg actcgtaccg cccctcgagg      60
ccagcgcgtt cacgctcgcg ctcgcgatcg ccgcctcgcg cgccggtgcc cgtgcggacg     120

| | |
|---|---|
| gaggaggaga agcaggcggc ggcaaaggcc gagtacgaga agctgctcaa catgcggtcg | 180 |
| ggcggcacgt acatcccgcc ggcgaggctg agggcgctgc aggcgcagat cacggacaag | 240 |
| agcagcaagg agtaccagcg gatggcgtgg gaggcgctca agaagagcat caacggcctg | 300 |
| atcaacaagg tcaacacggc caacatcaag cacattgtgc ccgagctgtt tggcgagaac | 360 |
| ctggtgcgcg ccgcggcct cttctgccgc tccatcatga aggcccaggc cgccagtttg | 420 |
| cccttcacgc ccatctacgc cgccatggcc gccattgtca acaccaagct gccgcaggtc | 480 |
| ggcgagctgc tggtcaagcg cctcatcatg cagttccgca agggcttcaa gcgcaacgac | 540 |
| aaggccgtct gtctgtcgtc gaccaccttc ctcgcccacc tcatcaacca gcaggtgcag | 600 |
| cacgagatgc tggccggcca gatcctgctg ctgctgctgc acaagccgac cgacgacagc | 660 |
| gtcgagattg ccgtgggctt ctgcaaggag gttggccagt acctcgagga gatgcagcct | 720 |
| gccatttcca tggccgtctt cgaccagttc cgcaacatcc tccacgagtc cgacattgac | 780 |
| aagcgaacgc agtacatgat tgaggtgctc ttccagatca ggaaggacaa gttcaaggat | 840 |
| cacccggcca tcaaggagga gctggacttg gtggaggagg aggaccagat cacgcacaag | 900 |
| gtggagcttg atggcgagat tgatgtgcag gacggactca acatcttcaa gtacgacccg | 960 |
| gagtgggagg agcatgagga ggcatacaag aggctcaagg cggagattct gggcgaagcc | 1020 |
| agcgatgacg aggagggcga cgaggacgag gacgaggacg agagctccga agatgaagaa | 1080 |
| aacgaagaga caaaggccat ggagatcaag gaccagtcta acgccgactt ggtcaaccta | 1140 |
| cggaggacca tctacctcac catcatgtcg agcgccgacc cagaggaagc agttcacaag | 1200 |
| ctgatgaaga tcaacctgcc cgtcggccag gaacccgagc tgccctcgat gattgtcgag | 1260 |
| tgttgctcgc aggagaagac gtacaccaag ttctttggct tgatcggcga gcgtttcgcc | 1320 |
| aagatcaatc ggctgtggtg cgacctcttt gagcaggcct ttgtcaagta ctacgagacg | 1380 |
| atccaccgat acgaaaacaa caagctgcgg aacattgcca tgctgtttgg ccacatgttt | 1440 |
| gcttccgacg ctctgggctg gcactgcctt tccgtcattc acctcaacga ggaggagacc | 1500 |
| acgtcgagca gccgcatctt catcaagatt ctgttccagc acatttccga ggaaatcggc | 1560 |
| ctggctaagc tccgggcacg catgactgac gagacgctgc ggcccagcct cgaaggcctc | 1620 |
| ttccccagag agaaccctcg caacatccga ttctccatca actacttcac cagcatcggc | 1680 |
| atgggtgtac tgaccgagga gatgcagagc cacctcatga acatgccaa gcctgcgctg | 1740 |
| cccgcccctg ctgctcagga ccgctcggat acggactccg tctcgagcta ttcgtcttac | 1800 |
| actcactcat catactcttc ccgctcgcgc tcacggtccc gatctgtggg tcgtcggagc | 1860 |
| ggcggtcgag gccgatcgct ttcccgaact ccgcctcgac gtggcgcaag gagccgatcc | 1920 |
| tactctgacg actcacggtc accgtcgcgg tcaagatcac gatcccgctc cgattccgtc | 1980 |
| tctactcgtg ggcgaaggcg agcgtcgtac tcggccagtc ctccccggcg tggtggccgt | 2040 |
| cgggttgcca gcagaagccg aagctactcg tcgggctcct cacggtctcc gccaccacgg | 2100 |
| aaccgcggtc gcgcacgaag caactcgtat agttcctaca gccgctctcc atcttcttca | 2160 |
| ccacgacgcg gcagagacgc agactcggcc agcccgcctc cgcgaagggg tcgaccgcgc | 2220 |
| cagagcccac caggcggtcc cgcaggtcga aggaacagtc cgtctgtcgg cagcggaggg | 2280 |
| ccccgcaaga agccccgacg ggacagccga tcgccgtctc gcgactattc gtcccggtcc | 2340 |
| ccgtctcggt cgccgtcgag atctcgatcc cctccgccgg ctgcgcgtgg ccgaagggc | 2400 |
| tcttatacgc cgtcacgcag ccgcagcccg cctccgcgca gggtgaggga tggctcgccg | 2460 |

```
ggtcgtctga ggggtgggag gtcgcctagt cctcctttgc cggtgaagag gaggcggtat    2520
gatagcgaga gtgtttctcg gtcgccgcct cctttgaagc gcgggagaag ggataactaa    2580
```

<210> SEQ ID NO 9
<211> LENGTH: 543
<212> TYPE: PRT
<213> ORGANISM: Trichoderma reesei

<400> SEQUENCE: 9

```
Met Thr Val Leu Thr Ser Pro Leu Ala Ser Tyr Asn Val Ala Asn Lys
1               5                   10                  15

Leu Tyr Lys Thr Thr Leu Leu Asn Thr Val Cys Leu Val Ala Gly Leu
            20                  25                  30

Ser Ile Phe Phe Phe Gly Tyr Asp Gln Gly Leu Met Gly Gly Val Asn
        35                  40                  45

Thr Thr Arg Asp Tyr Ala Glu Arg Met Gly Phe Gly His Trp Asp Glu
    50                  55                  60

Asp Gln Asn Ile Val Val Asp Lys Pro Leu Leu Gln Gly Gly Ile
65                  70                  75                  80

Val Ala Val Tyr Tyr Leu Pro Gly Thr Leu Cys Gly Cys Leu Leu Gly
                85                  90                  95

Gly Trp Leu Gly Asp Arg Tyr Gly Arg Ile Lys Thr Ile Ala Ile Ala
            100                 105                 110

Cys Ala Trp Ser Val Cys Ala Ala Ala Leu Gln Ala Ser Ala Met Asn
        115                 120                 125

Ala Asn Trp Met Phe Cys Ala Arg Val Leu Asn Gly Val Gly Thr Gly
    130                 135                 140

Ile Leu Asn Ala Ile Thr Pro Val Trp Ala Thr Glu Thr Ala Ala His
145                 150                 155                 160

Thr Ser Arg Gly Gln Phe Val Ser Ile Glu Phe Thr Leu Asn Ile Leu
                165                 170                 175

Gly Val Val Val Ala Tyr Trp Leu Glu Phe Gly Thr Ser Lys Tyr His
            180                 185                 190

Asp Asn Thr Ser Ser Phe Ile Trp Arg Phe Pro Val Ala Phe Gln Ile
        195                 200                 205

Leu Pro Leu Ile Leu Leu Phe Leu Ile Ile Trp Ile Met Pro Glu Ser
    210                 215                 220

Pro Arg Trp Leu Val Lys Val Gly Arg Glu Glu Ala Arg Phe Ile
225                 230                 235                 240

Leu Gly Arg Leu Arg Gly Asn Glu Gly Glu Asp Gly Leu Lys Ala Glu
                245                 250                 255

Ala Glu Tyr Asn Asp Ile Val Asn Ile His Lys Leu Glu Val Asp Thr
            260                 265                 270

Ala Lys Gln Gln Ser Tyr Phe Ser Met Phe Phe Gly Ile Gly Ser Gly
        275                 280                 285

Lys Leu His Thr Gly Arg Arg Val Gln Leu Val Ile Trp Leu Gln Ile
    290                 295                 300

Leu Gln Glu Trp Ile Gly Ile Ala Gly Ile Thr Ile Tyr Gly Pro Glu
305                 310                 315                 320

Ile Phe Thr Ile Ala Gly Ile Ser Ala Lys Asp Arg Leu Trp Val Ser
                325                 330                 335

Gly Ile Asn Asn Ile Thr Tyr Met Phe Ala Thr Leu Ile Cys Val Phe
            340                 345                 350

Thr Ile Asp Arg Ile Gly Arg Arg Trp Thr Leu Tyr Trp Gly Ala Val
```

```
                    355                 360                 365
Gly Gln Gly Ile Cys Met Phe Val Ala Gly Gly Leu Ala Arg Ala Thr
    370                 375                 380
Ile Asn Ala Ser Gly Lys Ala Ser Gln Ser His Ile Gly Gly Ala Ala
385                 390                 395                 400
Thr Phe Phe Val Phe Leu Tyr Thr Ala Ile Phe Gly Ala Thr Trp Leu
                405                 410                 415
Thr Val Pro Trp Leu Tyr Pro Ala Glu Ile Phe Pro Leu Gln Val Arg
            420                 425                 430
Ala Lys Gly Asn Ala Trp Gly Val Val Gly Trp Ser Ile Gly Asn Gly
        435                 440                 445
Trp Cys Val Leu Leu Pro Thr Ile Phe Lys Ala Leu Asn Glu Lys
    450                 455                 460
Thr Leu Tyr Ile Phe Gly Ala Val Asn Ala Leu Ser Ile Leu Val Val
465                 470                 475                 480
Trp Ala Leu Tyr Pro Glu Ser Asn Gln Arg Thr Leu Glu Glu Met Asp
                485                 490                 495
Leu Val Phe Ala Ser Asp Ser Ile Trp Ala Trp Glu Ala Glu Arg Asn
            500                 505                 510
Phe Ala Lys Leu Lys Ala Glu Asn Pro Asp Leu Val Gln Gly Ser Thr
        515                 520                 525
Asn His Gly Val Val Asp Ile Glu Gln Val Ala Glu Pro Lys Glu
    530                 535                 540

<210> SEQ ID NO 10
<211> LENGTH: 1870
<212> TYPE: DNA
<213> ORGANISM: Trichoderma reesei

<400> SEQUENCE: 10
atgaccgtcc tcacctcacc tctggccagc tataatgtgg ccaacaagct gtacaaaacc      60
actctgctca acaccgtctg cctcgtggcc ggactgtcga tcttcttctt cggctatgat     120
cagggattga tgggcggtgt taacacgacg cgcgactatg ccgagcgcat gggctttggc     180
cactgggacg aagaccagaa cattgtcgtc gtcgataagc cgctgctgca gggcggtatc     240
gtagctgtct actatctccc cggaacgctg tgcggttgtc tgcttggcgg ttggcttggt     300
gatcgctatg gccgtatcaa aacaattgcc attgcctgtg cgtggagtgt ctgcgcagcc     360
gccctgcagg cctcagctat gaatgcgaac tggatgtttt gcggtatgtc gatgattctt     420
ggacaatcac aaccgaacta ttactgatga tgagatgaaa cagcccgcgt tctgaacggc     480
gtcggcactg gaatcttgaa cgcaatcacg cctgtgtggg caaccgagac tgctgctcac     540
acttctcgag gccagttcgt ttccattgag ttcaccctca acattcttgg tgttgttgta     600
gcctactggc tggaattgta cgtgcctcct cactcaggat ccccagtctt gtggaaagtc     660
tccctaatgc ggtggcagtg gtacttctaa atatcacgac aacacatcct ccttcatctg     720
gagattcccg gtcgccttcc agatcctccc cctaatcctt ctgttcctca tcatctggat     780
catgcctgaa tcccccgct ggctcgtcaa agtgggtcgt gaagaagagg ctcgcttcat     840
ccttggtcgt ctccgtggca atgagggcga ggacggcctc aaggcggaag cagagtacaa     900
tgatattgtc aacatccaca agcttgaagt agacaccgcc aagcagcaga gctacttctc     960
catgttcttt ggcattgggt ctggaaagct acacactggc cggcgcgtgc agctggtcat    1020
ctggctccag atattgcaag agtggatcgg tattgcggga atcaccattt acggccctga    1080
```

```
gatctttacg attgctggca tcagcgcaaa ggacagactc tgggttagcg ggatcaacaa   1140
tatcacatac atggtacgtt tagccaacac ctcctcacct caaagattcc atcacactaa   1200
cacgggagca gttcgccaca ctgatctgcg tcttcaccat cgatcgcata ggtcgccgtt   1260
ggactctgta ctggggagct gtcggccagg gcatttgcat gttcgtcgcc ggtggcctcg   1320
ctcgcgcaac catcaatgcc tcaggcaaag caagccagag ccacatcggc ggcgctgcaa   1380
cattctttgt gttcctctac actgccattt tcggcgctac ctggctgacg gttccttggt   1440
tgtatccggc cgagattttc cctctgcagg ttagagccaa gggaaatgcc tggggtgtcg   1500
ttggctggtc cattggcaac ggctggtgtg taagtgcact tttcattctc ctctcccgtc   1560
tgggctcttc tggtctaatc ttctctaggt gctcctgctt cctacgatct tcaaggcgct   1620
caacgaaaag acactctaca tttttggcgc cgtcaacgcc ctgtccatcc tcgtcgtgtg   1680
ggctctgtac cccgaatcga atcaacgaac tctagaggag atggacctcg tctttgctag   1740
cgacagcatc tgggcctggg aggctgagcg taattttgcc aagctcaagg ctgaaaaccc   1800
ggatcttgtt cagggctcaa caaaccacgg agttgtagat attgagcaag ttgccgagcc   1860
aaaggagtag                                                          1870

<210> SEQ ID NO 11
<211> LENGTH: 735
<212> TYPE: PRT
<213> ORGANISM: Trichoderma reesei

<400> SEQUENCE: 11

Met Ala Val Asn Arg Ile Arg Gly Ala Phe Ala Ala Pro Arg Lys Gly
1               5                   10                  15

Glu Thr Phe Glu Leu Arg Ala Gly Leu Val Ser Gln Tyr Ala Tyr Glu
                20                  25                  30

Arg Lys Glu Ser Ile Gln Lys Thr Ile Met Ala Met Thr Leu Gly Lys
            35                  40                  45

Asp Val Ser Ala Leu Phe Pro Asp Val Leu Lys Asn Ile Ala Thr Ser
        50                  55                  60

Asp Leu Asp Gln Lys Lys Leu Val Tyr Leu Tyr Leu Met Asn Tyr Ala
65                  70                  75                  80

Lys Thr His Pro Asp Leu Cys Ile Leu Ala Val Asn Thr Phe Val Gln
                85                  90                  95

Asp Ser Glu Asp Pro Asn Pro Leu Val Arg Ala Leu Ala Ile Arg Thr
            100                 105                 110

Met Gly Cys Ile Arg Val Asp Lys Met Val Asp Tyr Met Glu Glu Pro
        115                 120                 125

Leu Arg Lys Thr Leu Arg Asp Glu Ser Pro Tyr Val Arg Lys Thr Ala
    130                 135                 140

Ala Ile Cys Val Ala Lys Leu Phe Asp Leu Asn Pro Ala Met Cys Ile
145                 150                 155                 160

Glu Asn Gly Phe Ile Glu Thr Leu Gln Glu Met Ile Gly Asp Pro Asn
                165                 170                 175

Pro Met Val Val Ala Asn Ser Val Gln Ala Leu Ala Glu Ile Ser Glu
            180                 185                 190

Thr Ala Pro Glu Thr Arg Ala Leu Val Thr Pro Pro Val Leu Lys
        195                 200                 205

Lys Leu Leu Met Ala Met Asn Glu Cys Thr Glu Trp Gly Arg Ile Thr
    210                 215                 220

Ile Leu Thr Val Leu Ala Asp Tyr Ala Ala Thr Asp Val Lys Glu Ser
```

-continued

```
                225                 230                 235                 240
Glu His Ile Cys Glu Arg Val Ile Pro Gln Phe Gln His Val Asn Pro
                        245                 250                 255
Ser Val Leu Ala Val Lys Val Phe Ile His Met Lys Ser
                260                 265                 270
Ile Asn Pro Glu Leu Val Arg Ser Tyr Leu Lys Lys Met Ala Pro Pro
                        275                 280                 285
Leu Val Thr Leu Val Ala Ser Ala Pro Glu Val Gln Tyr Val Ala Leu
            290                 295                 300
Arg Asn Ile Asp Leu Leu Gln Ala Lys Pro Asp Ile Leu Ser Lys
305                 310                 315                 320
Glu Leu Arg Val Phe Phe Cys Lys Tyr Asn Asp Pro Tyr Val Lys
                        325                 330                 335
Met Gln Lys Leu Glu Ile Met Val Arg Ile Ala Asn Glu Lys Asn Tyr
                340                 345                 350
Glu Gln Leu Leu Ser Glu Leu Lys Glu Tyr Ala Leu Glu Val Asp Met
                355                 360                 365
Asp Phe Val Arg Arg Ala Ile Lys Ala Ile Gly Gln Val Ala Ile Lys
            370                 375                 380
Ile Glu Glu Ala Ser Gly Lys Cys Val Gln Ala Leu Glu Asp Leu Leu
385                 390                 395                 400
Ala Thr Lys Val Asn Tyr Val Val Gln Glu Val Val Val Ile Lys
                        405                 410                 415
Asp Ile Leu Arg Lys Tyr Pro Gly Tyr Glu Gly Val Ile Pro Ser Leu
                420                 425                 430
Cys Asn Tyr Ile Asp Glu Leu Asp Glu Ala Asn Ala Arg Gly Ser Leu
            435                 440                 445
Ile Trp Ile Val Gly Glu Tyr Ala Glu Lys Ile Ser Asn Ala Glu Glu
            450                 455                 460
Ile Leu Glu Gly Phe Val Asp Thr Phe Leu Glu Glu Phe Thr Gln Thr
465                 470                 475                 480
Gln Leu Gln Ile Leu Thr Ala Val Val Lys Leu Phe Leu Lys Lys Pro
                        485                 490                 495
Ser Gly Ala Gln Gly Leu Val Gln Lys Val Leu Gln Glu Ala Thr Thr
                500                 505                 510
Asn Asn Asp Asn Pro Asp Ile Arg Asp Arg Ala Tyr Val Tyr Trp Arg
            515                 520                 525
Leu Leu Ser Gly Asp Leu Glu Val Ala Lys Asn Ile Val Leu Ser Gln
            530                 535                 540
Lys Pro Thr Ile Ser Thr Thr Met Thr Ser Leu Pro Thr Ala Leu Leu
545                 550                 555                 560
Glu Gln Leu Leu Ser Glu Leu Ser Thr Leu Ala Ser Val Tyr His Lys
                        565                 570                 575
Pro Pro Glu Ala Phe Val Gly Lys Gly Arg Phe Gly Ala Asp Glu Ile
                580                 585                 590
Gln Arg Ala Ala Ile Gln Glu Gln Arg Gln Asn Ala Ala Glu Asn Pro
            595                 600                 605
Ile Ala Ala Ser Val Ala Ala Ala Ala Asn Gly Ser Ser Ser Val
            610                 615                 620
Ser Gln Asn Asn Ile Glu Asn Leu Leu Asp Ile Asp Phe Asp Gly Ala
625                 630                 635                 640
Ala Pro Ala Ser Gln Glu Gln Asn Ser Ala Ala Gly Thr Pro Asp Arg
                        645                 650                 655
```

```
Val Ser Ser Pro Ala Thr Gly Gly Met Ala Asp Met Ser Met Phe
            660                 665                 670

Asp Ala Pro Pro Ala Gly Ser Ser Gly Gly Ala Pro Ser Gly Gly Met
        675                 680                 685

Asn Asp Leu Met Asn Gly Phe Glu Gly Leu Asn Phe Gly Ala Thr Ser
        690                 695                 700

Thr Asn Gln Pro Leu Pro Ala Ala Met Gln Leu His Asn Ala Gln Gly
705                 710                 715                 720

Gly Ser Gln Pro Lys Lys Asp Ser Asp Asp Leu Leu Gly Leu Leu
                725                 730                 735

<210> SEQ ID NO 12
<211> LENGTH: 2589
<212> TYPE: DNA
<213> ORGANISM: Trichoderma reesei

<400> SEQUENCE: 12
atggcggtga atcgcatccg gggcgccttt gccgcgcctc ggaagggaga gacattcgag    60
ctgcgggccg gcctggtgtc gcagtatgcc tacgagcgga aggagtccat ccagaagacc   120
atcatggcca tgacgctggg caaggacgtg tccgccctgt cccagacgt cttgaagaac    180 attgccacgt ccgacctgga ccagaagaag ctggtctacc tctacctcat gtatgtggct   240
gcagacaatg ccgaccatg atcacacaca cggagcgaag gacgagatac tgcctgacgt    300
ggcgatgcgg tgctaacgtg gagtgtgacc ccaggaacta cgcaaagaca cacccagacc   360
tctgcattct cgccgtcaac acgttcgtgc aagactcgga gacccgaac cgctggtgc    420 gagcgctggc catccgcaca atgggctgca tccgggtgga caagatggtc gactacatgg   480
aggagccgct gcggaagacg ctgcgggacg agtcgccgta cgtgcgcaag acggccgcca   540
tctgcgtggc caagctgttc gacctgaacc cggccatgtg catcgagaac ggcttcatcg   600
agacgctgca ggagatgatt ggcgacccga accccatggt ggtcgcaaac tcggtccagg   660
cgctggccga gattagcgag acggcgcccg agacgcgggc gctgctggtg acgccccgg   720 tgctcaagaa gctgcttatg gccatgaacg aatgcaccga atggggtaga atcaccattc   780
tgaccgtgct ggcagactac gctgccaccg acgtcaagga gtcggagcac atctgcgaga   840
gggtcattcc gcagttccag cacgtcaacc ctagcgtggc cctggctgct gtcaaggtgg   900
tctttattca tatgaagtcg attaacccgg agctcgtgcg gtcatatctt aagaagatgg   960
cgcctccact cggtgcgttc cgatcatgtc cccgatttga catctgagaa gacatgacgt  1020
gactatgcta acactgcagc ttgtatacag tcacactggt tgcttctgcc cccgaggtcc  1080
aatacgtcgc tctcagaaac attgatctgc tccttcaagc caagcccgac atcctgagca  1140
aagagttaag agtcttcttt tgcaaataca acgacccgcc gtacgtcaag atgcaaaagc  1200
tggaaatcat ggtcaggata gcaaacgaaa agaactacga gcagctcctg tctgagctca  1260
aggaatacgc cctggaagtg gacatggact ttgtgcgccg agccatcaag gccatcggcc  1320
aggtggccat caagattgag gaggccagtg gcaagtgcgt gcaggcgctg gaagatcttc  1380
tcgctaccaa ggtcaactac gtggtgcaag aggttgtcgt ggtcatcaaa gatatcctgc  1440
gaaagtaccc cggttacgag ggcgtgatcc cctcgctctg caactacatt gacgagctcg  1500
acgaggccaa tgctcgtgga tccctcatct ggattgtggg agagtacgcc gagaagatta  1560
gcaacgctga ggagattctg gagggttttg tagacacctt tttggaggag ttcactcagg  1620
tatgtggaga gctgtggaaa agtcggggat tttggctaat cgaactgcag acacaactcc  1680
```

```
agatccttac agctgttgtt aagctgtttt tgaagaagcc gagtggcgcg cagggcctgg    1740
ttcagaaggt gctgcaggag gcaacaacca acaacgacaa ccccgatatc cgcgacagag    1800
catacgtcta ctggcgattg ttatcgggag atttggaggt ggccaaggta ggagtcgttg    1860
gcgtcctttg atgagagctg cgcatactga cggatctcaa gaacattgtc ctgtcacaga    1920
agccgaccat ttcaacaaca atgacaagcc tgccgactgc gctactggag cagctgctgt    1980
cggagctgtc aactctggcg tcggtatacc acaagccccc ggaagccttt gtcggcaagg    2040
gccggttcgg tgccgacgag atccagcgag ccgccatcca ggagcagcgc cagaacgccg    2100
cggaaaaccc catcgccgca tccgtggctg ccgccgccgc caatggctcc tcgtcggtct    2160
cgcaaaacaa cattgagaac ctgctggaca ttgactttga cggcgcagca ccggcctctc    2220
aggagcagaa cagcgcggcg ggaacacctg accgggtgtc gagcccggcc acgggtggca    2280
tggccgacat gatgagcatg tttgatgcgc ctccggctgg cagctctgga ggtgctccgt    2340
ccggcggcat gaacgacttg atgaacggat ttgaggggct caactttggg gccacgagta    2400
caaatcagcc gttgccggcg gcgatgcagc tgcacaatgc gcaaggcggc tctcagccga    2460
agaaggatag cgatgatctt tgggttttgt tgtaaatgtt ggaggagcgt atatgcatgc    2520
aagcagcaag ccagaagggg agaagaatcg acaagagaga ctggaggagg aggcaaggga    2580
ggggggggg                                                            2589

<210> SEQ ID NO 13
<211> LENGTH: 5634
<212> TYPE: DNA
<213> ORGANISM: Artificial Sequence
<220> FEATURE:
<223> OTHER INFORMATION: DNA fragment for transformation

<400> SEQUENCE: 13
cttaagactg aaagtaggtg gcaatctggg ttgtgcgtcc atggcgggca tcaagggctg      60
catgggcagt tgatcttcgc atgggatcac caaccttcat ctctgcttgg ccatgatagg     120
ctgcttgtgt gtatcacgga ggaatactct gaaccgacgt ggtagaacat tcaagtccgg     180
gctagccccg tgtagcccca aaggcagctt gagctttgaa tctgtctgga accgggaagc     240
atgggggagg gaagcaagg aactggcaag gaataggaca gaaacgcaca gacgcagaaa      300
aaagggacag gaatggaact ctcctttgct ccgtatctcc tgattgagac agatggggga     360
tggggatgag acgccgccga cgtaagactg cgagctacca aaggcagctt agcacggacg     420
agctggataa agggttcatg tgccattgct ttttttgtca tgtgaaagtc gagctgttgg     480
tgatgcagct gtcaaaggga gagaaggaca gagggagggg cactttgacg agaaggctgt     540
cgtgcttttc ccctgcagga tcaatcgaac aaacaaacaa acaaagatgg tgttcgtcat     600
tgttctcatt gattctgctt cttccgtcct tcactccatc ttctattgcc tagcctcacg     660
tcctcctcct gtgttaccgt actagaaggc ctgtcagcaa gccaccaata caggcctttg     720
ttattatggg gggacttctc atctcacccc tcaggtaaga tcgatctaaa gtacctggta     780
atgatgcgcc cagcctagtg gactgacagc agtactggct ttgtctggct gctgaagacg     840
aggcatctgg ttggtgcttt tgtggtgata tctcgaatgt tccgcattca gcctctggtc     900
ttggccaacg tagctttgct actgctgcaa cattcacctt ggtgagtctc caattggacg     960
gtgagtatca actggggaag cctcagctgt ccacttgaac ggtcaattgt atctgcgtag    1020
ccagtgattg gtagatgggc ttgcttggat tcatcaacct ccttcaccag ccctgctgct    1080
```

```
ctttgtcaag tctctctcct cctctttgtc gtgctaccta cagcagtatt acgtacaggg    1140
cgctccccgt attacctaag tccctatctc ggcagcggcc gcctagtcat cattggatag    1200
gcagattact cagcctgaat gacatcaaca tgttacccat gatacaatag gtcacacaaa    1260
caagcgctaa gatgcacttg gtatgacaag cccagtagtc cgtttcaaaa gacctagatg    1320
atgaactaca acatgaggtg ttgcctcctg atccagtcca actgcaaacg ctgatgtata    1380
ctcaatcaag cctgatgtaa atgctgcgac tcgattcgct ggatatgaag atcaaagaga    1440
gctctgatgg gtccaatata gccgggtttt gttaggacag tccaccacac cgatattaga    1500
attggtcaag caccttatca tttcatagag attgcggttt ctagatctac gccaggaccg    1560
agcaagccca gatgagaacc gacgcagatt tccttggcac ctgttgcttc agctgaatcc    1620
tggcaatacg agatacctgc tttgaatatt ttgaatagct cgcccgctgg agagcatcct    1680
gaatgcaagt aacaaccgta gaggctgaca cggcaggtgt tgctagggag cgtcgtgttc    1740
tacaaggcca gacgtcttcg cggttgatat atatgtatgt ttgactgcag gctgctcagc    1800
gacgacagtc aagttcgccc tcgctgcttg tgcaataatc gcagtgggga agccacaccg    1860
tgactcccat ctttcagtaa agctctgttg gtgtttatca gcaatacacg taatttaaac    1920
tcgttagcat ggggctgata gcttaattac cgtttaccag tgccgcggtt ctgcagcttt    1980
ccttggcccg taaaattcgg cgaagccagc caatcaccag ctaggcacca gctaaaccct    2040
ataattagtc tcttatcaac accatccgct cccccgggat caatgaggag aatgaggggg    2100
atgcggggct aaagaagcct acataaccct catgccaact cccagtttac actcgtcgag    2160
ccaacatcct gactataagc taacacagaa tgcctcaatc ctgggaagaa ctggccgctg    2220
ataagcgcgc ccgcctcgca aaaaccatcc ctgatgaatg gaaagtccag acgctgcctg    2280
cggaagacag cgttattgat ttcccaaaga aatcgggcat cctttcagag gccgaactga    2340
agatcacaga ggcctccgct gcagatcttg tgtccaagct ggcggccgga gagttgacct    2400
cggtggaagt tacgctagca ttctgtaaac gggcagcaat cgcccagcag ttagtagggt    2460
cccctctacc tctcagggag atgtaacaac gccaccttat gggactatca agctgacgct    2520
ggcttctgtg cagacaaact gcgcccacga gttcttccct gacgccgctc tcgcgcaggc    2580
aagggaactc gatgaatact acgcaaagca caagagaccc gttggtccac tccatggcct    2640
ccccatctct ctcaaagacc agcttcgagt caaggtacac cgttgcccct aagtcgttag    2700
atgtcccttt ttgtcagcta acatatgcca ccagggctac gaaacatcaa tgggctacat    2760
ctcatggcta acaagtacg acgaaggggga ctcggttctg acaaccatgc tccgcaaagc    2820
cggtgccgtc ttctacgtca agacctctgt cccgcagacc ctgatggtct gcgagacagt    2880
caacaacatc atcgggcgca ccgtcaaccc acgcaacaag aactggtcgt gcggcggcag    2940
ttctggtggt gagggtgcga tcgttgggat tcgtggtggc gtcatcggtg taggaacgga    3000
tatcggtggc tcgattcgag tgccggccgc gttcaacttc ctgtacgtc taaggccgag    3060 tcatgggcgg ctgccgtatg caaagatggc gaacagcatg gagggtcagg agacggtgca    3120
cagcgttgtc gggccgatta cgcactctgt tgagggtgag tccttcgcct cttccttctt    3180
ttcctgctct ataccaggcc tccactgtcc tcctttcttg cttttatac tatatacgag    3240 accggcagtc actgatgaag tatgttagac ctccgcctct tcaccaaatc cgtcctcggt    3300
caggagccat ggaaatacga ctccaaggtc atcccatgc cctggcgcca gtccgagtcg    3360
gacattattg cctccaagat caagaacggc gggctcaata tcggctacta caacttcgac    3420
ggcaatgtcc ttccacaccc tcctatcctg cgcggcgtgg aaaccaccgt cgccgcactc    3480
```

```
gccaaagccg gtcacaccgt gaccccgtgg acgccataca agcacgattt cggccacgat   3540
ctcatctccc atatctacgc ggctgacggc agcgccgacg taatgcgcga tatcagtgca   3600
tccggcgagc cggcgattcc aaatatcaaa gacctactga acccgaacat caaagctgtt   3660
aacatgaacg agctctggga cacgcatctc cagaagtgga attaccagat ggagtacctt   3720
gagaaatggc gggaggctga agaaaaggcc gggaaggaac tggacgccat catcgcgccg   3780
attacgccta ccgctgcggt acggcatgac cagttccggt actatgggta tgcctctgtg   3840
atcaacctgc tggatttcac gagcgtggtt gttccggtta cctttgcgga taagaacatc   3900
gataagaaga atgagagttt caaggcggtt agtgagcttg atgccctcgt gcaggaagag   3960
tatgatccgg aggcgtacca tggggcaccg gttgcagtgc aggttatcgg acggagactc   4020
agtgaagaga ggacgttggc gattgcagag gaagtgggga agttgctggg aaatgtggtg   4080
actccatagc taataagtgt cagatagcaa tttgcacaag aaatcaatac cagcaactgt   4140
aaataagcgc tgaagtgacc atgccatgct acgaaagagc agaaaaaaac ctgccgtaga   4200
accgaagaga tatgacacgc ttccatctct caaaggaaga atcccttcag ggttgcgttt   4260
ccagtctaga cgcgttcttc ttcaaccaag agttgtccaa ggggatactg tcgcttgtac   4320
ctccagacaa ccctgtacac agagatggtt tgtcacacga aacaatcagg acgatacgct   4380
attcatggga gacgatgaaa ctgacaatga gggcttcaag tcatgacact ccagggcgaa   4440
atggtgaggc aggcagaaat gctgcgctcg ctcgacgagc cgcacgagcc tgtctattcc   4500
gccaggcaac agttcttcgg cacggtcgac aacgccccg tgtccccgcg gcagcttcct    4560
caagacgaca acaggcgagt cacgctcaac gttccgcagg gccggagtca gccgtcgtac   4620
cgaccagccg tcccctcgaa cctgtccgcc ggcacgcggc gacccctacgg atccatcagc   4680
ggcggtgccg gctcctcacc tctgcgcaat gccgcgccgg caccccagc agggccgcat    4740
ccccttttcca acgtggagac cgtccccagc aacctggcca gacgccatac cgccgcagac   4800
attcgcgcac acgatggca gcccaacgca ccgccttatc ccctggagc cgtgccgccg    4860
cccgtatggc ctcaatctcc caatcggccc gaggatcaga ggataagaga ctctctctct   4920
tcgtttttccc tgcaggcccc atcggctcat ggacacccgc actcgcggcc ggcgacgcca   4980
ccccacgctc ccttttcaaa cggcgcgagc ggagggtcgg ataccttttgg cagctggtcg   5040
tggggcgcgg catcgaaccg cgagagcaag acgattggag cgttgaagga gtcgtcagcg   5100
ccgcccacca ggaggggcag catggcacac atcctcaacc ccagcgatac cgctgagcga   5160
tcagacgagg acgaggaccc ccggggcgac gacgacagaa agcgaaaacg aagacagtga   5220
tgccgcgccg tgtagcgttg aagaaaagag ggggactgga tcatggccat ggcacatgat   5280
tttggcgctg gttacaacaa ggagtctctt taatccaggc tggcgttttt ttcgaaatat   5340
ccctgctccg cactggttcc tggatgtctt caggtttcca tccgttgcgt tttcattcct   5400
tctaccgcat ctttgtctca tttcccgaca tttcagattg gatatcttgg cgctgcagta   5460
agtctgtaag ctatgctcat tgatgacggc ctcggagaat acactttcgc ctttacgcct   5520
tgattgtata ttagcacata ttcctgaacc ggatcatggc cataggcttg gcaccacacg   5580
tccctcaaca aatgcggaca aaagttgctg tatcaaggaa tcgtcgatac tagt           5634
```

<210> SEQ ID NO 14
<211> LENGTH: 37
<212> TYPE: DNA
<213> ORGANISM: Artificial Sequence
<220> FEATURE:

<223> OTHER INFORMATION: Oligo DNA for PCR

<400> SEQUENCE: 14
atgcatctta agactgaaag taggtggcaa tctgggt                            37

<210> SEQ ID NO 15
<211> LENGTH: 35
<212> TYPE: DNA
<213> ORGANISM: Artificial Sequence
<220> FEATURE:
<223> OTHER INFORMATION: Oligo DNA for PCR

<400> SEQUENCE: 15
atgcggccgc tgccgagata gggacttagg taata                              35

<210> SEQ ID NO 16
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 16
atacgcgttc ttcttcaacc aagagttgtc caa                                33

<210> SEQ ID NO 17
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 17
atactagtat cgacgattcc ttgatacagc aac                                33

<210> SEQ ID NO 18
<211> LENGTH: 5385
<212> TYPE: DNA
<213> ORGANISM: Artificial Sequence
<220> FEATURE:
<223> OTHER INFORMATION: DNA fragment for transformation

<400> SEQUENCE: 18
cttaagatgc tgcaccaagt tgctatgaat catggggctg actatgactg atgcatttgt      60
ggtatgatat atagacgcac caccttgtag tgtccagtag tatcatcttt tactaccaca     120
atcaatgaga tatgaagaga cgaagacgca actcagcaga acagaagcat gccctgctga     180
ctcagcaggc tgcgggtgac gacaacgatc ccccttggc tgcgttatgg tttcatggct      240
gcatctctcc aaaactcaga agagaacaaa gagccaggca gccggccagc tacctattct     300
acctacctac cttacttgac cacctaatga aactcaccaa cattccaccc tctgcaacca     360
ttctgtacct cctcaattga tgtgctcctt gtgataccc gatttatcct tgcaatcctg      420
ttgattgcgc atttgattga ttgatgaatt gattgattgc tcctaccttt gatacccttc     480
atcacaccat gggccaagcc ccttctcaga cgcggcggac tcggcggacg cacgaggaac     540
tgacacagga gcttgtgagc gcgccgttgc accttggcct gggaacaagc aagggcctag     600
gctttgctaa ctgtgcgtga acaggcgtac agattcaagg aaaagtgctt cacgtcgctg     660
gagtactact cactgaagga tgtcttcaag aaactggccg accagcaggg cgacatacgg     720
tatctcaagg aggacaccat agctcgcttc ctcgagatcc cagacatcct cggggcttcg     780
ccggtcatct tccacatgat ctcgtatctg ggtgcgtttc cctttctgca ggaggccccc     840

```
gtggtgctcg agctggcgca gttgatcatg gtcgttgtca tcatgacgga gcgatataag    900
cgcgttcttg cgaagggctc gacagacagg acgaaattat tttttaaaag cttggctgtg    960
tatgaccgga aagtgatgga ggagaccggt tcttcaccgc ggaattccac ttcaaaagac   1020
gccactgcga ggccgagcgc caacacaaga ggctttgcaa tcgacgagcc gatggccgag   1080
gacgaggatg atggcgacga cgacgacgat gatcttgtca ttagcggccg cctagtcatc   1140
attggatagg cagattactc agcctgaatg acatcaacat gttacccatg atacaatagg   1200
tcacacaaac aagcgctaag atgcacttgg tatgacaagc ccagtagtcc gtttcaaaag   1260
acctagatga tgaactacaa catgaggtgt tgcctcctga tccagtccaa ctgcaaacgc   1320
tgatgtatac tcaatcaagc ctgatgtaaa tgctgcgact cgattcgctg gatatgaaga   1380
tcaaagagag ctctgatggg tccaatatag ccggttttg ttaggacagt ccaccacacc    1440
gatattagaa ttggtcaagc accttatcat ttcatagaga ttgcggtttc tagatctacg   1500
ccaggaccga gcaagcccag atgagaaccg acgcagattt ccttggcacc tgttgcttca   1560
gctgaatcct ggcaatacga gatacctgct ttgaatattt tgaatagctc gcccgctgga   1620
gagcatcctg aatgcaagta acaaccgtag aggctgacac ggcaggtgtt gctagggagc   1680
gtcgtgttct acaaggccag acgtcttcgc ggttgatata tatgtatgtt tgactgcagg   1740
ctgctcagcg acgacagtca agttcgccct cgctgcttgt gcaataatcg cagtggggaa   1800
gccacaccgt gactcccatc tttcagtaaa gctctgttgg tgtttatcag caatacacgt   1860
aatttaaact cgttagcatg gggctgatag cttaattacc gtttaccagt gccgcggttc   1920
tgcagctttc cttggcccgt aaaattcggc gaagccagcc aatcaccagc taggcaccag   1980
ctaaacccta taattagtct cttatcaaca ccatccgctc ccccgggatc aatgaggaga   2040
atgaggggga tgcggggcta agaagccta cataaccctc atgccaactc ccagtttaca    2100
ctcgtcgagc caacatcctg actataagct aacacagaat gcctcaatcc tgggaagaac   2160
tggccgctga taagcgcgcc cgcctcgcaa aaccatccc tgatgaatgg aaagtccaga    2220
cgctgcctgc ggaagacagc gttattgatt tcccaaagaa atcgggcatc ctttcagagg   2280
ccgaactgaa gatcacagag gcctccgctg cagatcttgt gtccaagctg gcggccggag   2340
agttgacctc ggtggaagtt acgctagcat tctgtaaacg ggcagcaatc gcccagcagt   2400
tagtagggtc ccctctacct ctcagggaga tgtaacaacg ccaccttatg ggactatcaa   2460
gctgacgctg gcttctgtgc agacaaactg cgcccacgag ttcttccctg acgccgctct   2520
cgcgcaggca agggaactcg atgaatacta cgcaaagcac aagagacccg ttggtccact   2580
ccatggcctc cccatctctc tcaaagacca gcttcgagtc aaggtacacc gttgccccta   2640
agtcgttaga tgtcccttt tgtcagctaa catatgccac cagggctacg aaacatcaat    2700
gggctacatc tcatggctaa acaagtacga cgaaggggac tcggttctga caaccatgct   2760
ccgcaaagcc ggtgccgtct tctacgtcaa gacctctgtc ccgcagaccc tgatggtctg   2820
cgagacagtc aacaacatca tcgggcgcac cgtcaaccca cgcaacaaga actggtcgtg   2880
cggcggcagt tctggtggtg agggtgcgat cgttgggatt cgtggtggcg tcatcggtgt   2940
aggaacggat atcggtggct cgattcgagt gccggccgcg ttcaacttcc tgtacggtct   3000
aaggccgagt catgggcggc tgccgtatgc aaagatggcg aacagcatgg agggtcagga   3060
gacggtgcac agcgttgtcg ggccgattac gcactctgtt gagggtgagt ccttcgcctc   3120
ttccttcttt tcctgctcta taccaggcct ccactgtcct cctttcttgc tttttatact   3180
```

```
atatacgaga ccggcagtca ctgatgaagt atgttagacc tccgcctctt caccaaatcc   3240
gtcctcggtc aggagccatg gaaatacgac tccaaggtca tccccatgcc ctggcgccag   3300
tccgagtcgg acattattgc ctccaagatc aagaacggcg ggctcaatat cggctactac   3360
aacttcgacg gcaatgtcct tccacaccct cctatcctgc gcggcgtgga aaccaccgtc   3420
gccgcactcg ccaaagccgg tcacaccgtg accccgtgga cgccatacaa gcacgatttc   3480
ggccacgatc tcatctccca tatctacgcg gctgacggca cgccgacgt aatgcgcgat   3540
atcagtgcat ccggcgagcc ggcgattcca aatatcaaag acctactgaa cccgaacatc   3600
aaagctgtta acatgaacga gctctgggac acgcatctcc agaagtggaa ttaccagatg   3660
gagtaccttg agaaatggcg ggaggctgaa gaaaaggccg ggaaggaact ggacgccatc   3720
atcgcgccga ttacgcctac cgctgcggta cggcatgacc agttccggta ctatgggtat   3780
gcctctgtga tcaacctgct ggatttcacg agcgtggttg ttccggttac cttttgcggat  3840
aagaacatcg ataagaagaa tgagagtttc aaggcggtta gtgagcttga tgccctcgtg   3900
caggaagagt atgatccgga ggcgtaccat ggggcaccgg ttgcagtgca ggttatcgga   3960
cggagactca gtgaagagag gacgttggcg attgcagagg aagtggggaa gttgctggga   4020
aatgtggtga ctccatagct aataagtgtc agatagcaat ttgcacaaga aatcaatacc   4080
agcaactgta aataagcgct gaagtgacca tgccatgcta cgaaagagca gaaaaaaacc   4140
tgccgtagaa ccgaagagat atgacacgct tccatctctc aaaggaagaa tcccttcagg   4200
gttgcgtttc cagtctagac gcgtagagtg tgtactagca tccttcgtcg atgtcgagac   4260
gtcgccaggc attggatata cccggttcaa gactgtcatt ccgtcctat tccccaacct   4320
ctttgctggg ttcaatggcc tgtttgaaca cttctttttc tccaaggatc tggacttctc   4380
gaagcacaag gttgagaagc ctggtgacga gcagctcatc attggcaaga ttgcgcaacc   4440
tctgctccca accctggcg acatcatgac tgagcatacg ctgtcgcaac tttcactgtt   4500
tctacctggc tcctctctgt tccgaagagt gagattgctc tattcgggaa acgatgctgg   4560
attctccatg ggcagcctcc agaccaaggt ctttaactgg agagcccaa ccattcttct   4620
agtcagcgga tcgagattag cagacgtccc cgagggaggc caagaggcat cgttcgcctc   4680
ttcgcttccc accaaacggt tccctcatgg tagtaaatcc gagcgtgtaa cgtttggcgt   4740
gtacgttcga gagccttgga agcacacgca caaagagtgc ttcggcaatt cggaaacaat   4800
actcttttcaa ctagaaccca ttcacgatgt tttccctgcc tctacaatca atacagacta   4860
cgtcaccttc acgaaaccac ctggcaaccg gccctgtcta gcatttgggt gcccacaccc   4920
caaaccgacg cagtcgcatc gcaaggaggg catacatgct ttaggagccg tgtctctgtt   4980
gtttgatgaa tctttcgagt tcggagtctt caatcatgac tacaagtcga gggggcgc   5040
tttccacact agcatcgtga ggaaatatga ttttcaggat cggtttcgaa tcgagaacat   5100
ggaagtctgg ggatgtggtg gtgacgagga ggccaaggcg caagcagaga gatgggcttg   5160
ggaagaacgt gaagcggaag cccgtcgcag gatcaacctt gggacgggtg acattgaggc   5220
ggacagggca ttgctggaga tggccgggct agtaggaggg aatcgcagcg gcggttcaat   5280
gggttgaatg gatgatcacg gaatgatacg atgtaaactt ctgtgttcta ggtcgcgggc   5340
actggattct cccctgatat catgatatgc ttttgggtaa ctagt            5385
```

<210> SEQ ID NO 19
<211> LENGTH: 1131
<212> TYPE: DNA
<213> ORGANISM: Artificial Sequence

```
<220> FEATURE:
<223> OTHER INFORMATION: Synthetic gene for transformation

<400> SEQUENCE: 19
cttaagatgc tgcaccaagt tgctatgaat catggggctg actatgactg atgcatttgt    60
ggtatgatat atagacgcac caccttgtag tgtccagtag tatcatcttt tactaccaca   120
atcaatgaga tatgaagaga cgaagacgca actcagcaga acagaagcat gccctgctga   180
ctcagcaggc tgcgggtgac gacaacgatc cccctttggc tgcgttatgg tttcatggct   240
gcatctctcc aaaactcaga agagaacaaa gagccaggca gccggccagc tacctattct   300
acctacctac cttacttgac cacctaatga aactcaccaa cattccaccc tctgcaacca   360
ttctgtacct cctcaattga tgtgctcctt gtgataccc gatttatcct tgcaatcctg    420
ttgattgcgc atttgattga ttgatgaatt gattgattgc tcctacctt gatcccttc     480
atcacaccat gggccaagcc ccttctcaga cgcggcggac tcggcggacg cacgaggaac   540
tgacacagga gcttgtgagc gcgccgttgc accttggcct gggaacaagc aagggcctag   600
gctttgctaa ctgtgcgtga acaggcgtac agattcaagg aaaagtgctt cacgtcgctg   660
gagtactact cactgaagga tgtcttcaag aaactggccg accagcaggg cgacatacgg   720
tatctcaagg aggacaccat agctcgcttc ctcgagatcc cagacatcct cggggcttcg   780
ccggtcatct tccacatgat ctcgtatctg ggtgcgtttc cctttctgca ggaggccccc   840
gtggtgctcg agctggcgca gttgatcatg gtcgttgtca tcatgacgga gcgatataag   900
cgcgttcttg cgaagggctc gacagacagg acgaaattat tttttaaaag cttggctgtg   960
tatgaccgga aagtgatgga ggagaccggt tcttcaccgc ggaattccac ttcaaaagac  1020
gccactgcga ggccgagcgc caacacaaga ggctttgcaa tcgacgagcc gatggccgag  1080
gacgaggatg atggcgacga cgacgacgat gatcttgtca ttagcggccg c           1131

<210> SEQ ID NO 20
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 20
atacgcgtag agtgtgtact agcatccttc gtc                                33

<210> SEQ ID NO 21
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 21
atactagtta cccaaaagca tatcatgata tca                                33

<210> SEQ ID NO 22
<211> LENGTH: 5859
<212> TYPE: DNA
<213> ORGANISM: Artificial Sequence
<220> FEATURE:
<223> OTHER INFORMATION: DNA fragment for transformation

<400> SEQUENCE: 22
cttaagtctg atgatgaaca aatggctcaa gggcatgcat gcaacccggg aaatgaccat    60
```

| | |
|---|---|
| ccctgctcta cacgaaagac acacaagaaa aaagggaggc gtcccgtcca actgggttcc | 120 |
| cgctttgcgc tagtaatcag gctttttttt tctcgacatg ccaacaaagc cagtgtttct | 180 |
| caactgtatc gattattagt ggaaaattcg ccaaggccga ggtgacatgc tcccggagca | 240 |
| gcgaaaagca gctgggacaa agttgtggca ctttgacgcc aatagcggga cccgggatac | 300 |
| atatgtagga agcaggcgat gcgggagact gtgtacgagc gacgactggg ttccctgacg | 360 |
| gatagtatca gttgtccgag aagccatgtt tacccattc tgctgacggt gttttgttg | 420 |
| ggtgggtgtt gttcttcaga ggacatgcgg agagcgcaag tcagcgacgg gaccgcggat | 480 |
| aactccgaca agccttgtcc taggagttca gcgttcttgt ttcctgatta tagtataacc | 540 |
| gcgacagcag aacacctctt gtctctagag tctatcgcgg ggagggagtc tctgagggta | 600 |
| agctgtggga gctgacatct agtctgcctt tttagtcccg ggctttgaga tgcggcatta | 660 |
| cccgatggtg atgagagatg acttgttcta ctcaaggaaa aatgacagat gcttagtagc | 720 |
| aaaagttggc cgaagctacc ttgctaccta acctgaagga ttttttgccg ccttttggca | 780 |
| acttcacaca cacggagatc cttgtctagc tgcgtctcta gttcagcttc ttggtggact | 840 |
| aaatcaagag gaagtcctcc actgggcaca ataggccgct tggagaagga tagatccgtg | 900 |
| aggcctagtc tgctgatcgg aagatacctg atcacctaag agacgtgagc gttaggatcc | 960 |
| aagatttgct agatcccatc aactgttaat ggcgcgacga tgctactgtt tgatgcgcag | 1020 |
| cggctgagcc ttggccaatc tatggccgtt tttgccggaa gctggatgcc gtcaaagggg | 1080 |
| tttgctattt gaggcgggtg actgcagagg atgggcacaa ttgagcagta ctcgtacacc | 1140 |
| acaaaagata taaggtacct agcgaagggt gaagccaggc gggacgaggc actagtgggc | 1200 |
| aaatggtctg ttccggataa tctctctgca ctgttgggtt ggttcgtctc acaggcattt | 1260 |
| gacttgatga aggctcctga gctattgatc gtgctcctag catggtcgtg acaggagcag | 1320 |
| cagggacgga tgaaggctca ttggctgaca gtgagttggt gaactgtgat tatgacgatg | 1380 |
| ttttgttttc ggcagagcat ggatggtaag tgcttatctc ggcggccgcc tagtcatcat | 1440 |
| tggataggca gattactcag cctgaatgac atcaacatgt tacccatgat acaataggtc | 1500 |
| acacaaacaa gcgctaagat gcacttggta tgacaagccc agtagtccgt ttcaaaagac | 1560 |
| ctagatgatg aactacaaca tgaggtgttg cctcctgatc cagtccaact gcaaacgctg | 1620 |
| atgtatactc aatcaagcct gatgtaaatg ctgcgactcg attcgctgga tatgaagatc | 1680 |
| aaagagagct ctgatgggtc aatatagcc gggttttgtt aggacagtcc accacaccga | 1740 |
| tattagaatt ggtcaagcac cttatcattt catagagatt gcggtttcta gatctacgcc | 1800 |
| aggaccgagc aagcccagat gagaaccgac gcagatttcc ttggcacctg ttgcttcagc | 1860 |
| tgaatcctgg caatacgaga tacctgcttt gaatattttg aatagctcgc cgctggaga | 1920 |
| gcatcctgaa tgcaagtaac aaccgtagag gctgacacgg caggtgttgc tagggagcgt | 1980 |
| cgtgttctac aaggccagac gtcttcgcgg ttgatatata tgtatgtttg actgcaggct | 2040 |
| gctcagcgac gacagtcaag ttcgccctcg ctgcttgtgc aataatcgca gtggggaagc | 2100 |
| cacaccgtga ctcccatctt tcagtaaagc tctgttggtg tttatcagca atacacgtaa | 2160 |
| tttaaactcg ttagcatggg gctgatagct taattaccgt ttaccagtgc cgcggttctg | 2220 |
| cagctttcct tggcccgtaa aattcggcga agccagccaa tcaccagcta ggcaccagct | 2280 |
| aaaccctata attagtctct tatcaacacc atccgctccc ccgggatcaa tgaggagaat | 2340 |
| gaggggggatg cggggctaaa gaagcctaca taaccctcat gccaactccc agtttacact | 2400 |
| cgtcgagcca acatcctgac tataagctaa cacagaatgc ctcaatcctg ggaagaactg | 2460 |

```
gccgctgata agcgcgcccg cctcgcaaaa accatccctg atgaatggaa agtccagacg    2520
ctgcctgcgg aagacagcgt tattgatttc ccaaagaaat cgggcatcct ttcgagaggcc   2580 gaactgaaga tcacagaggc ctccgctgca gatcttgtgt ccaagctggc ggccggagag    2640
ttgacctcgg tggaagttac gctagcattc tgtaaacggg cagcaatcgc ccagcagtta    2700
gtagggtccc ctctacctct cagggagatg taacaacgcc accttatggg actatcaagc    2760
tgacgctggc ttctgtgcag acaaactgcg cccacgagtt cttccctgac gccgctctcg    2820
cgcaggcaag ggaactcgat gaatactacg caaagcacaa gagacccgtt ggtccactcc    2880
atggcctccc catctctctc aaagaccagc ttcgagtcaa ggtacaccgt tgcccctaag    2940
tcgttagatg tccctttttg tcagctaaca tatgccacca gggctacgaa acatcaatgg    3000
gctacatctc atggctaaac aagtacgacg aaggggactc ggttctgaca accatgctcc    3060
gcaaagccgg tgccgtcttc tacgtcaaga cctctgtccc gcagaccctg atggtctgcg    3120
agacagtcaa caacatcatc gggcgcaccg tcaacccacg caacaagaac tggtcgtgcg    3180
gcggcagttc tggtggtgag ggtgcgatcg ttgggattcg tggtggcgtc atcggtgtag    3240
gaacggatat cggtggctcg attcgagtgc cggccgcgtt caacttcctg tacggtctaa    3300
ggccgagtca tgggcggctg ccgtatgcaa agatggcgaa cagcatggag ggtcaggaga    3360
cggtgcacag cgttgtcggg ccgattacgc actctgttga gggtgagtcc ttcgcctctt    3420
ccttcttttc ctgctctata ccaggcctcc actgtcctcc tttcttgctt tttatactat    3480
atacgagacc ggcagtcact gatgaagtat gttagacctc cgcctcttca ccaaatccgt    3540
cctcggtcag gagccatgga aatacgactc caaggtcatc cccatgccct ggcgccagtc    3600
cgagtcggac attattgcct ccaagatcaa gaacggcggg ctcaatatcg gctactacaa    3660
cttcgacggc aatgtccttc cacaccctcc tatcctgcgc ggcgtggaaa ccaccgtcgc    3720
cgcactcgcc aaagccggtc acaccgtgac cccgtggacg ccatacaagc acgatttcgg    3780
ccacgatctc atctcccata tctacgcggc tgacggcagc gccgacgtaa tgcgcgatat    3840
cagtgcatcc ggcgagccgg cgattccaaa tatcaaagac ctactgaacc cgaacatcaa    3900
agctgttaac atgaacgagc tctgggacac gcatctccag aagtggaatt accagatgga    3960
gtaccttgag aaatggcggg aggctgaaga aaaggccggg aaggaactgg acgccatcat    4020
cgcgccgatt acgcctaccg ctgccggtacg gcatgaccag ttccggtact atgggtatgc    4080
ctctgtgatc aacctgctgg atttcacgag cgtggttgtt ccggttacct ttgcggataa    4140
gaacatcgat aagaagaatg agagtttcaa ggcggttagt gagcttgatg ccctcgtgca    4200
ggaagagtat gatccggagg cgtaccatgg ggcaccggtt gcagtgcagg ttatcggacg    4260
gagactcagt gaagagagga cgttggcgat tgcagaggaa gtggggaagt tgctgggaaa    4320
tgtggtgact ccatagctaa taagtgtcag atagcaattt gcacaagaaa tcaataccag    4380
caactgtaaa taagcgctga agtgaccatg ccatgctacg aaagagcaga aaaaaacctg    4440
ccgtagaacc gaagagatat gacacgcttc catctctcaa aggaagaatc ccttcagggt    4500
tgcgtttcca gtctagacgc gtcatttctc ctgtttctga atcccaagcg ccattgtctc    4560
cgccacctac tcctaaatcg ccccctgtgc cttcgacggt tcttcatgac tggttcaaac    4620
aagggttcga gttcaagggc cacggtcacg ataccatatt gtcagttgct ttggacaatt    4680
cgctcacctc gctctacaca cttggggagg accctctaca caccgcgaac gaagcgtcct    4740
ccacgacgag cccctgggct gaacacgggg cgagggagat tcctgggcgc cgaacccgct    4800
```

-continued

```
tcatcatcgc tggaaccaac tccggcgcgg tgcttgtctg aatgcgcgt gatgacgatc    4860 gaactcgtga tatacaacca ctgcgcatcc ttcagaccga gtcaccagag gtttctgctg    4920
tggcagcctc tgggttgtat ctcgttcacg gcggcagcga cggccttgtc caagcctggg    4980
atcccttggc atctcaaacg gatcccatca gaacgattaa cgctcggtca aatggccggg    5040
tcccccgtca catgctggta atgaatccg cattgcagga ggagacatac tcggcagcaa    5100
aggccatata tcttgaccct gattctacga cgcttcaagg tgtagtctct tttggcgcat    5160
tcctgcgata ttggtcgtat gggtccaatg gtcatgccac aggtcgcaag cggcgcgtcc    5220
gacacgccga tatggacgct cggcttgcga gtcgccggca aggccatgca gtgtcaggct    5280
acattgcctc tgaggaagcc gagatgcgac gggaggatga gcagcaggct cgcgagcaca    5340
accgtcgtct caagagattt ggcgctctag gcgacttgac cgaggaagaa gcgcttctct    5400
acgcccagat ggtctcccaa gaggcgtacc acgtagagga gcagcgacgg gccagcgatt    5460
cggcagccga cgccagcctg gacaccgcct cttcctttag cgagaatacc gtcgagactc    5520
tgacacctga tccgagcgtc gccgatccgg tcgcttcgga aacgagcggc atggccgagg    5580
atgacgagta cgagcagcag attcagcagg ctatacgtct gtctctgcta gaaggcgtca    5640
acaacggcgt ggaacagtca cctgtggatt cctcacgggg caacagctct gttgatttcg    5700
accaaccggt caatgtcaag tacaagccca agggcgggaa gaaggggaag caatcagggg    5760
cttcttctgg tggctcaccg tctgcgagcc acacgcccgt tggtggtggt gcttcttctt    5820
cgcggctgag cacgactgaa gatgaggatt tagctcgag                           5859
```

<210> SEQ ID NO 23
<211> LENGTH: 37
<212> TYPE: DNA
<213> ORGANISM: Artificial Sequence
<220> FEATURE:
<223> OTHER INFORMATION: Oligo DNA for PCR

<400> SEQUENCE: 23
atgcatctta agtctgatga tgaacaaatg gctcaag                             37

<210> SEQ ID NO 24
<211> LENGTH: 35
<212> TYPE: DNA
<213> ORGANISM: Artificial Sequence
<220> FEATURE:
<223> OTHER INFORMATION: Oligo DNA for PCR

<400> SEQUENCE: 24
atgcggccgc cgagataagc acttaccatc catgc                               35

<210> SEQ ID NO 25
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 25
atacgcgtca tttctcctgt ttctgaatcc caa                                 33

<210> SEQ ID NO 26
<211> LENGTH: 32
<212> TYPE: DNA
<213> ORGANISM: Artificial Sequence
<220> FEATURE:
<223> OTHER INFORMATION: Oligo DNA for PCR

```
<400> SEQUENCE: 26
actcgagcta aatcctcatc ttcagtcgtg ct                                32

<210> SEQ ID NO 27
<211> LENGTH: 46
<212> TYPE: DNA
<213> ORGANISM: Trichoderma reesei

<400> SEQUENCE: 27
gcgcacgtgt gccggtcgcg cggctacaag ctggtcatct acatgc                 46
```